(12) United States Patent
Hayzelden

(10) Patent No.: US 11,285,299 B2
(45) Date of Patent: Mar. 29, 2022

(54) MOLD FOR FORMING SOLDER DISTAL TIP FOR GUIDEWIRE

(71) Applicant: ABBOTT CARDIOVASCULAR SYSTEMS INC., Santa Clara, CA (US)

(72) Inventor: Robert C. Hayzelden, Murrieta, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 176 days.

(21) Appl. No.: 16/671,057

(22) Filed: Oct. 31, 2019

(65) Prior Publication Data

US 2021/0128884 A1  May 6, 2021

(51) Int. Cl.
| | | |
|---|---|---|
| *A61M 25/09* | (2006.01) | |
| *B23K 1/08* | (2006.01) | |
| *B22D 18/02* | (2006.01) | |
| *B21F 15/08* | (2006.01) | |
| *B23K 3/08* | (2006.01) | |
| *B23K 101/32* | (2006.01) | |
| *C23C 6/00* | (2006.01) | |
| *B22D 19/04* | (2006.01) | |

(52) U.S. Cl.
CPC ............ *A61M 25/09* (2013.01); *B23K 1/08* (2013.01); *A61M 2025/09083* (2013.01); *A61M 2025/09108* (2013.01); *A61M 2025/09175* (2013.01); *B21F 15/08* (2013.01); *B22D 18/02* (2013.01); *B22D 19/04* (2013.01); *B23K 3/085* (2013.01); *B23K 2101/32* (2018.08); *C23C 6/00* (2013.01)

(58) Field of Classification Search
CPC ........ A61M 25/09; A61M 2025/09175; A61M 2025/09083; A61M 2025/09108; B23K 1/08; B23K 2101/32; B23K 3/085; B22D 19/04; B22D 18/02; C23C 6/00; B21F 15/08; B21F 45/008
See application file for complete search history.

(56) References Cited

U.S. PATENT DOCUMENTS

| | | | |
|---|---|---|---|
| 3,612,058 A | * | 10/1971 | Ackerman ...... A61M 25/09033 600/585 |
| 4,716,757 A | | 1/1988 | McGregor et al. |
| 5,259,393 A | | 11/1993 | Corso et al. |
| 5,345,945 A | | 9/1994 | Hodgson et al. |
| 5,392,778 A | | 2/1995 | Horzewski |
| 5,454,788 A | * | 10/1995 | Walker .................... A61L 29/04 604/103 |
| 5,865,767 A | | 2/1999 | Frechette et al. |
| 5,951,496 A | * | 9/1999 | Willi .................... A61M 25/09 600/585 |
| 6,139,511 A | | 10/2000 | Huter et al. |
| 6,248,082 B1 | | 6/2001 | Jafari |

(Continued)

FOREIGN PATENT DOCUMENTS

| | | | | |
|---|---|---|---|---|
| EP | 2937109 A1 | 10/2015 | | |
| JP | 07255856 A | * 10/1995 | ............ | A61M 25/01 |
| JP | 2007089901 A | * 4/2007 | ............ | A61M 25/09 |

*Primary Examiner* — Sean P Dougherty
(74) *Attorney, Agent, or Firm* — Fulwider Patton LLP

(57) ABSTRACT

A mold is used to form a solder joint to join the distal end of the guidewire to a wire coil. The mold has a cavity that can have different configurations so that the solder joint can be any of bullet shaped, micro-J shaped, cone shaped, truncated cone shaped, or have a textured surface.

11 Claims, 21 Drawing Sheets

(56) References Cited

U.S. PATENT DOCUMENTS

| | | | |
|---|---|---|---|
| 6,379,369 B1* | 4/2002 | Abrams | A61L 31/022 |
| | | | 606/159 |
| 6,502,606 B2 | 1/2003 | Klint | |
| 6,666,829 B2 | 12/2003 | Cornish et al. | |
| 6,669,652 B2 | 12/2003 | Anderson et al. | |
| 6,673,025 B1 | 1/2004 | Richardson et al. | |
| 6,832,715 B2 | 12/2004 | Eungard et al. | |
| 7,077,811 B2 | 7/2006 | Vrba et al. | |
| 7,651,578 B2 | 1/2010 | Sharrow et al. | |
| 7,831,297 B2 | 11/2010 | Opie et al. | |
| 7,867,176 B2 | 1/2011 | Wu et al. | |
| 7,972,282 B2 | 7/2011 | Clark et al. | |
| 7,998,088 B2 | 8/2011 | Vrba et al. | |
| 8,262,588 B2 | 9/2012 | Miyata et al. | |
| 8,308,660 B2 | 11/2012 | Cornish et al. | |
| 8,414,506 B2 | 4/2013 | Reynolds et al. | |
| 8,585,612 B2 | 11/2013 | Nishigishi | |
| 8,585,613 B2 | 11/2013 | Nagano et al. | |
| 8,603,011 B2 | 12/2013 | Landowski | |
| 8,608,670 B2 | 12/2013 | Matsumoto et al. | |
| 8,622,432 B2 | 1/2014 | Bloomberg | |
| 8,622,932 B2 | 1/2014 | Matsumoto et al. | |
| 8,622,933 B2 | 1/2014 | Maki et al. | |
| 8,652,119 B2 | 2/2014 | Nishigishi | |
| 8,740,815 B2 | 6/2014 | Palme, Jr. et al. | |
| 8,758,269 B2 | 6/2014 | Miyata et al. | |
| 8,852,126 B2 | 10/2014 | Miyata et al. | |
| 8,951,210 B2 | 2/2015 | Miyata et al. | |
| 8,952,126 B2 | 2/2015 | Myles et al. | |
| 8,956,310 B2 | 2/2015 | Miyata et al. | |
| 8,961,434 B2 | 2/2015 | Miyata et al. | |
| 9,017,268 B2 | 4/2015 | Miyata et al. | |
| 9,028,428 B2 | 5/2015 | Maki | |
| 9,126,021 B2 | 9/2015 | Kanazawa | |
| 9,295,813 B2 | 3/2016 | Kanazawa et al. | |
| 9,295,815 B2 | 3/2016 | Stevens et al. | |
| 9,352,131 B2 | 5/2016 | Brown | |
| 9,492,641 B2 | 11/2016 | Edamatsu | |
| 9,522,256 B2 | 12/2016 | Takada | |
| 9,586,029 B2 | 3/2017 | Shekalim et al. | |
| 9,682,221 B2 | 6/2017 | Seaver et al. | |
| 9,770,574 B2 | 9/2017 | McArthur et al. | |
| 9,814,864 B2 | 11/2017 | Scarpine et al. | |
| 10,029,076 B2 | 7/2018 | Eskuri | |
| 10,279,150 B2 | 5/2019 | Nabeshima et al. | |
| 2003/0102360 A1* | 6/2003 | Eungard | A61M 25/09 |
| | | | 228/224 |
| 2003/0125642 A1* | 7/2003 | Kato | A61M 25/09033 |
| | | | 600/585 |
| 2004/0122340 A1* | 6/2004 | Vrba | A61M 25/09 |
| | | | 600/585 |
| 2005/0038359 A1* | 2/2005 | Aimi | A61M 25/09 |
| | | | 600/585 |
| 2012/0310217 A1* | 12/2012 | Maki | A61M 25/09 |
| | | | 604/528 |
| 2013/0006149 A1* | 1/2013 | Purtzer | B23K 35/30 |
| | | | 600/585 |
| 2013/0110002 A1* | 5/2013 | Miyata | A61M 25/09 |
| | | | 600/585 |
| 2013/0289445 A1 | 10/2013 | Edamatsu | |
| 2014/0180141 A1* | 6/2014 | Millett | A61B 5/6851 |
| | | | 600/486 |
| 2015/0075744 A1* | 3/2015 | Hofmann | B22D 18/06 |
| | | | 164/65 |
| 2016/0001048 A1 | 1/2016 | Koike | |
| 2017/0136207 A1* | 5/2017 | Shiono | A61M 25/0009 |
| 2018/0236581 A1* | 8/2018 | Simpson | B23K 35/3013 |

* cited by examiner

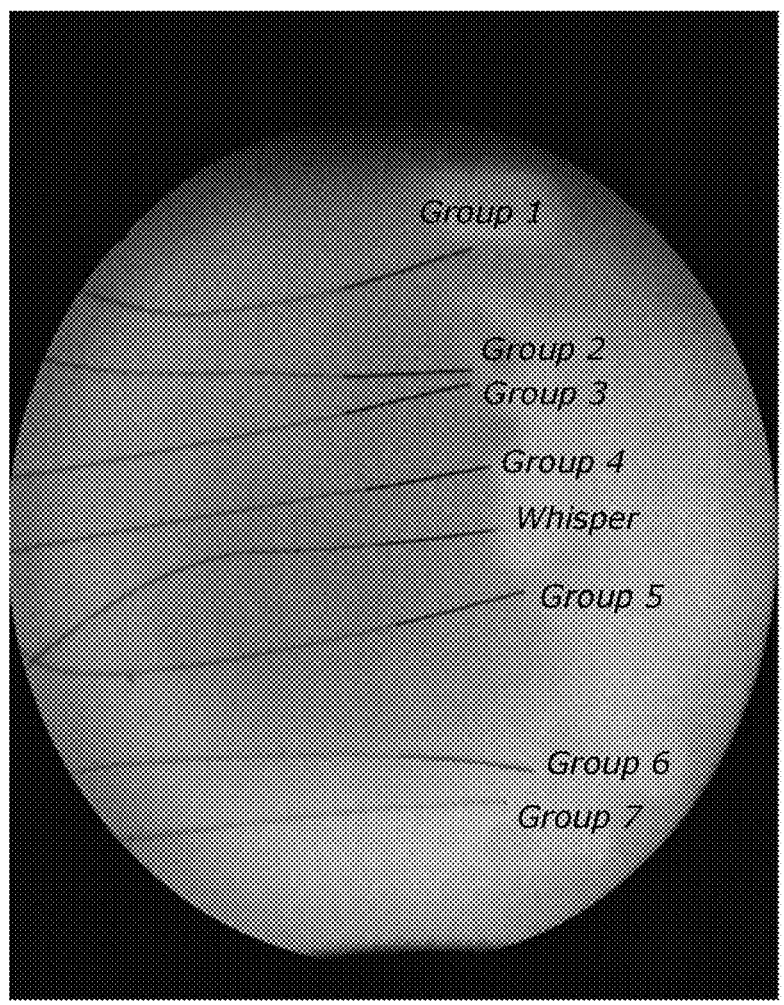
FIG. 6
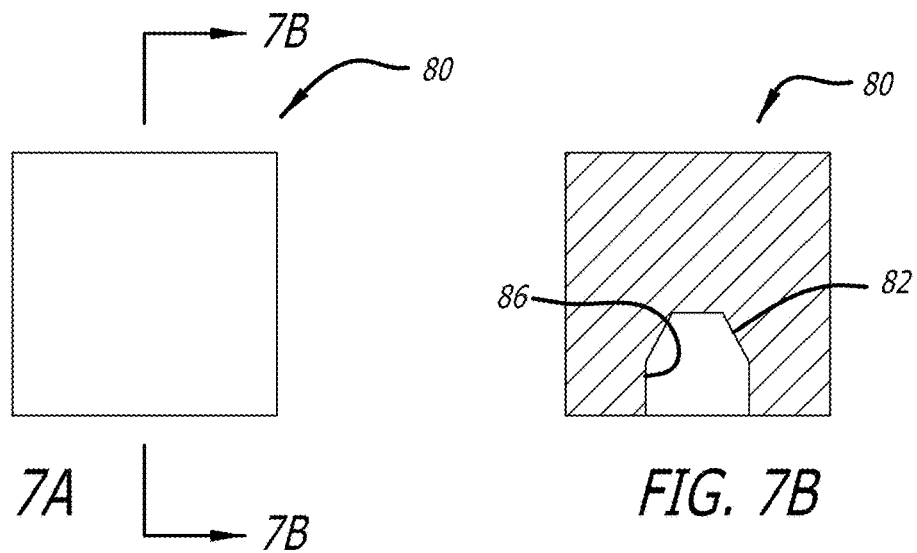
FIG. 7A
FIG. 7B

| Elastic Modulus (E), GPa | Yield Strength ($\sigma_y$), MPa | Ultimate strength ($\sigma_{ult}$), MPa |
|---|---|---|
| 193 | 2160 | 2390 |

FIG. 15A
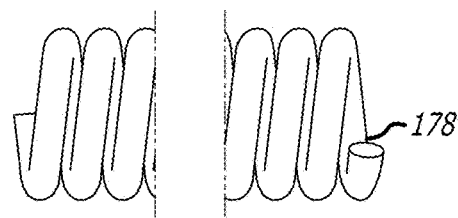
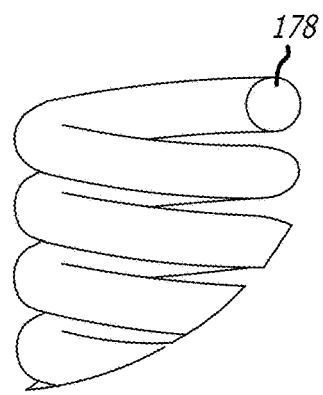
FIG. 15B
FIG. 16A
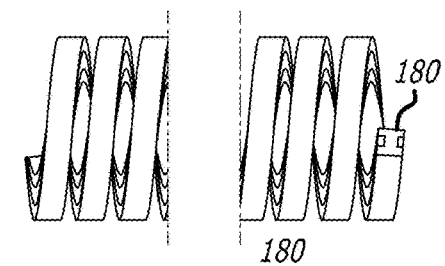
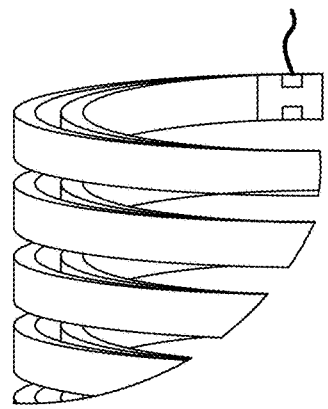
FIG. 16B
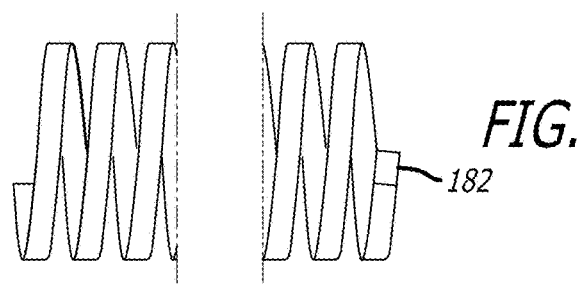
FIG. 17A
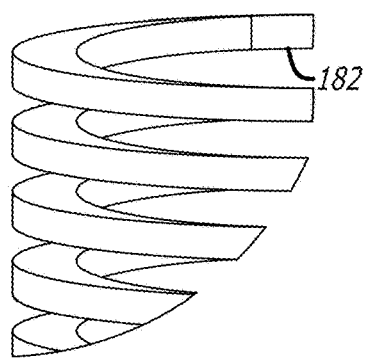
FIG. 17B

MOLD FOR FORMING SOLDER DISTAL TIP FOR GUIDEWIRE

BACKGROUND

This invention relates to the field of guidewires for advancing intraluminal devices such as stent delivery catheters, balloon dilatation catheters, atherectomy catheters and the like within body lumens.

In a typical coronary procedure a guiding catheter having a preformed distal tip is percutaneously introduced into a patient's peripheral artery, e.g., femoral or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the second is a bare wire technique which is used primarily for rapid exchange type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g., a lesion to be dilated or a dilated region where a stent is to be deployed. The catheter, which is slidably mounted onto the guidewire, is advanced out of the guiding catheter into the patient's coronary anatomy over the previously introduced guidewire until the operative portion of the intravascular device, e.g., the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location. For example, in the event of arterial blockage due to dissected lining collapse, a rapid exchange type perfusion balloon catheter can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rapid exchange (RX) catheter is mounted onto the proximal portion of the guidewire which extends out of the proximal end of the guiding catheter, which is outside of the patient. The catheter is advanced over the guidewire, while the position of the guidewire is fixed, until the operative means on the RX catheter is disposed within the arterial location where the procedure is to be performed. After the procedure, the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapeable member, which may be the distal extremity of the core member or a separate shaping ribbon, which is secured to the distal extremity of the core member, extends through the flexible body and is secured to the distal end of the flexible body by soldering, brazing or welding which forms a rounded distal tip. Torqueing means are provided on the proximal end of the core member to rotate, and thereby steer, the guidewire while it is being advanced through a patient's vascular system.

For certain procedures, such as when delivering stents around a challenging take-off, e.g., a shepherd's crook, tortuosities or severe angulation, substantially more support and/or vessel straightening is frequently needed from the guidewire than normal guidewires can provide. Guidewires have been commercially introduced for such procedures which provide improved distal support over conventional guidewires, but such guidewires are not very steerable and in some instances are so stiff that they can damage vessel linings when advanced therethrough. What has been needed and heretofore unavailable is a guidewire which provides a high level of distal support with acceptable steerability and little risk of damage when advanced through a patient's vasculature.

In addition, conventional guidewires using tapered distal core sections as discussed above can be difficult to use in many clinical circumstances because they have an abrupt stiffness change along the length of the guidewire, particularly where the tapered portion begins and ends. As a guidewire having a core with an abrupt change in stiffness is moved through tortuous vasculature of a patient, the physician moving the guidewire can feel the abrupt resistance as the stiffness change is deflected by the curvature of the patient's vasculature. The abrupt change in resistance felt by the physician can hinder the physician's ability to safely and controllably advance the guidewire through the vasculature. What has been needed is a guidewire that does not have an abrupt change in stiffness, particularly in the portions of the distal section that are subject to bending in the vasculature and guiding catheter. The present invention satisfies these and other needs by providing distal tip integrity, kink resistance, enhanced torque response, improved distal tip radiopacity, and a smooth transition region.

SUMMARY OF THE INVENTION

In one embodiment of the invention a guidewire has a radiopaque inner coil and a substantially non-radiopaque outer coil. The inner coil and the outer coil are attached to the distal end of the guidewire and the outer coil covers the inner coil and extends proximally along the guidewire proximal of a proximal end of the inner coil. The inner coil is formed from a radiopaque material so that the physician can easily detect the location of the distal end of the guidewire under fluoroscopy during a procedure. Both the inner coil and the outer coil can be formed from a single strand of wire or a multifilar strand of wire.

In another embodiment, a mold is used for forming a solder distal tip or solder joint at the distal end of the guidewire. The solder distal tip attaches the distal end of the guidewire and the distal end of the inner coil and the distal end of the outer coil (if present) together. It is important that the solder distal tip be uniform from one guidewire to the next, and repeatable in structural formation. A mold, including a split mold, provides a bullet shaped solder tip or a micro-J shape tip at the distal end of the guidewire to attach the inner and outer coils to the guidewire. Other shapes of solder tips are contemplated such as cone shape, truncated cone shape, and a solder joint having a textured surface.

In another embodiment, a laser is used to form dimples on the solder joint connecting the distal end of the guidewire. A laser is used to form dimples on the distal end of the solder joint such that the dimples resemble the dimples on a golf ball and can have specific spacing and patterns. The laser can be programmed to provide dimples that are spaced apart and have specific diameters and depths depending on the requirements of the user.

In another embodiment, the present invention guidewire increases the torquability of the guidewire without negatively affecting the bending stiffness and functionality of the guidewire by using different cross-section shapes of the coils. For example, the different cross-section shapes of the coils can include I-beam, vertical rectangular, vertical ellipse, square, peanut shape, vertical hexagonal, horizontal hexagonal, and horizontal ellipse cross-sections. Considering the constraints due to manufacturing, dimensions, and tolerances, the I-beam, peanut shape, vertical rectangular and vertical ellipse shaped cross-sections are more favorable than a conventional round cross-section coil, for increasing torquability without negatively affecting the bending stiffness of the guidewire. The different cross-section shaped coils can be used to form a single wire coil or a multifilar coil.

In another embodiment a guidewire tip shaping tool forms a micro-J shape in the distal tip of the guidewire. The shaping tool is provided to the physician with the guidewire so that the physician can select the amount of bend in the distal end of the guidewire using the shaping tool. Traditionally, the physician would bend the distal end of the guidewire with his/her hands, which lacked control of the bend angle and shape of the bend. The shaping tool includes a number of cavities having a different angular orientation and depth so that the physician can select the length of the bend and the angle of the bend in the distal tip of the guidewire. The shaping tool is spring loaded toward the open position so that the guidewire distal end can be inserted into a cavity. Once the guidewire is inserted into a cavity, the physician gently presses the ends of the shaping tool to overcome the spring force and shift an inner tube having the cavity relative to an outer tube to form the bend in the distal tip of the guidewire. The predetermined angle and length of the cavities provide a consistent micro-J shape for the physician to use.

In another embodiment of the invention, the distal section of the guidewire is reduced in cross-section to be more flexible when navigating tortious vessels. In this embodiment, a parabolic distal section of the guidewire includes a significant portion of the distal section having been ground down to form a continuous taper. The continuous taper is formed by a parabolic grind along the distal section of the guidewire. The parabolic grind provides a smooth curvilinear transition along the distal section of the guidewire that is highly flexible and yet maintains a linear change in stiffness thereby providing excellent torque and tactical feedback to the physician when advancing the guidewire through tortuous anatomy.

BRIEF DESCRIPTION OF THE DRAWINGS

FIG. 6 is a graph depicting the guidewires shown in FIG. 5 and showing the radiopacity of the distal portion of the guidewires including the coils.

FIG. 7A is an elevational view of a mold for forming a solder joint on the distal end of a guidewire.

FIG. 7B is a cross-sectional view taken along lines 7B-7B of the mold of FIG. 7A.

FIGS. 15A and 15B are elevational and front views of a prior art coil having a circular or round cross-section.

FIGS. 16A and 16B are elevational and front views respectively, of a coil having an I-beam cross-section.

FIGS. 17A and 17B are elevational and front views respectively, of a coil having a vertical rectangular cross-section.

DETAILED DESCRIPTION OF THE PREFERRED EMBODIMENTS

Prior Art Guidewires

Figure 1:
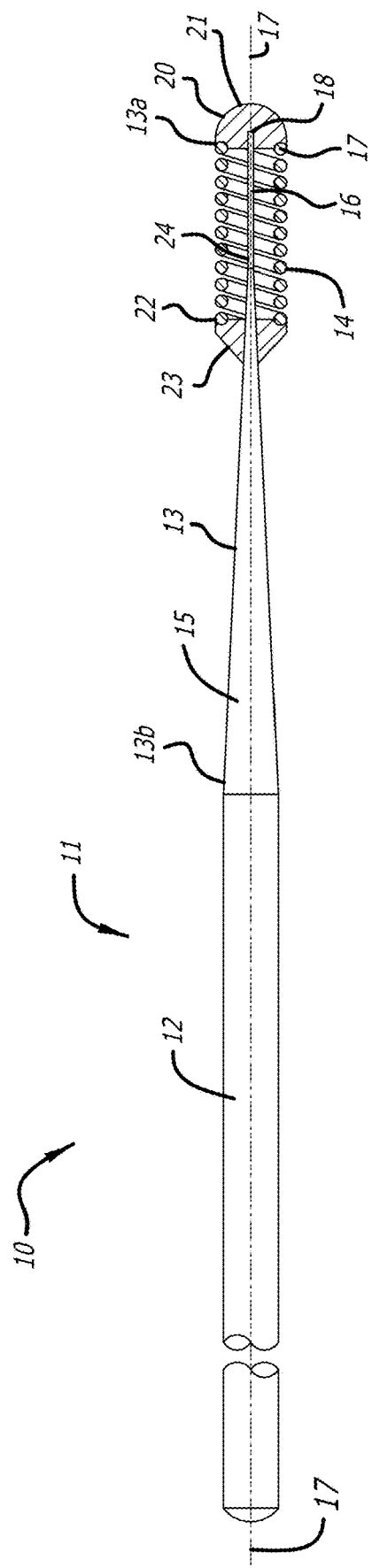
FIG. 1 is an elevational view of a prior art guidewire depicting a coil at the distal end of the guidewire.

Prior art guidewires typically include an elongated core wire having a flexible atraumatic distal end. A prior art guidewire is shown in FIG. 1 and includes an elongated core member 11 with a proximal core section 12, a distal core section 13, and a flexible body member 14 which is fixed to the distal core section. The distal core section 13 has a tapered segment 15, a flexible segment 16 which is distally contiguous to the tapered segment 15, a distal end 13a, and a proximal end 13b. The distal section 13 may also have more than one tapered segment 15 which have typical distally decreasing tapers with substantially round transverse cross sections.

The core member 11 may be formed of stainless steel, NiTi alloys or combinations thereof. The core member 11 is optionally coated with a lubricious coating such as a fluoropolymer, e.g., TEFLON® available from DuPont, which extends the length of the proximal core section. Hydrophilic coatings may also be employed. The length and diameter of prior art guidewire 10 may be varied to suit the particular procedures in which it is to be used and the materials from which it is constructed. The length of the guidewire 10 generally ranges from about 65 cm to about 320 cm, more typically ranging from about 160 cm to about 200 cm, and preferably from about 175 cm to about 190 cm for the coronary anatomy. The guidewire diameter generally ranges from about 0.008 inch to about 0.035 inch (0.203 to 0.889 mm), more typically ranging from about 0.012 inch to about 0.018 inch (0.305 to 0.547 mm), and preferably about 0.014 inch (0.336 mm) for coronary anatomy.

The flexible segment 16 terminates in a distal end 18. Flexible body member 14, preferably a coil, surrounds a portion of the distal section of the elongated core 13, with a distal end 19 of the flexible body member 14 secured to the distal end 18 of the flexible segment 16 by the body of solder 20. The proximal end 22 of the flexible body member 14 is similarly bonded or secured to the distal core section 13 by a body of solder 23. Materials and structures other than solder may be used to join the flexible body 14 to the distal core section 13, and the term "solder body" includes other materials such as braze, epoxy, polymer adhesives, including cyanoacrylates and the like.

The wire from which the flexible body 14 is made generally has a transverse diameter of about 0.001 to about 0.004 inch, preferably about 0.002 to about 0.003 inch (0.05 mm). Multiple turns of the distal portion of the coil may be expanded to provide additional flexibility. The coil may have a diameter or transverse dimension that is about the same as the proximal core section 12. The flexible body member 14 may have a length of about 2 to about 40 cm or more, preferably about 2 to about 10 cm in length. A flexible body member 14 in the form of a coil may be formed of a suitable radiopaque material such as platinum or alloys thereof or formed of other material such as stainless steel and coated with a radiopaque material such as gold.

The flexible segment 16 has a length typically ranging about 1 to about 12 cm, preferably about 2 to about 10 cm, although longer segments may be used. The form of taper of the flexible segment 16 provides a controlled longitudinal variation and transition in flexibility (or degree of stiffness) of the core segment. The flexible segment is contiguous with the core member 11 and is distally disposed on the distal section 13 so as to serve as a shapeable member.

Guidewire Having Radiopaque Inner Coil

In keeping with the invention, in one embodiment shown in FIGS. 2-6, a guidewire 30 has an elongated core member 32 with a proximal core section 34 and a distal core section 36. The distal core section 36 is preferably tapered, having a tapered segment 38 that tapers to a smaller diameter moving from the proximal end 40 of the guidewire toward the distal end 42 of the guidewire. The elongated core member 32 is preferably formed from stainless steel, however, it also can be formed from other metals or metallic alloys known in the art.

In order to improve radiopacity, the guidewire 30 shown in FIGS. 2-6 includes a radiopaque inner coil 44 positioned over the elongated core member at the distal end 42 thereof. The inner coil 44 may be 3 cm in length and have a distal end 46 that is coterminous with the distal end 42 of the elongated core member 32. While 3 cm is a preferred length for the radiopaque inner coil 44, the length of the inner coil 44 can range from 0.5 cm to 15 cm as necessary to satisfy the needs of the physician. The radiopaque inner coil 44 has a proximal end 48 with multiple coils 50 extending from the proximal end 48 to the distal end 46. The radiopaque inner coil 44 is made from a radiopaque material taken from the group of radiopaque metals including platinum (Pt), palladium (Pd), iridium (Ir), tungsten (W), tantalum (Ta), rhenium (Re) and gold (Au). In one embodiment, shown in FIG. 2, the radiopaque inner coil 44 is formed from a single filar coil 50 of wire, and the diameter can vary as required for a balance in radiopacity, flexibility, torquability and kink resistance (durability). In another embodiment, shown in FIG. 3, the radiopaque inner coil 44 is formed from a four filar coil 52 of wire. The four filar coil 52 can be made with drawn, filled tubing (tube filled radiopaque material or sandwiched) which is known in the prior art. The inner coil 44 can be formed using any number of filars, such as the eight filar coil shown in FIGS. 4A and 4B. In one embodiment, the eight filar coil of FIGS. 4A and 4B is 31 cm long, has an outer diameter of 0.0135±0.0005 inch, an inner diameter of 0.0095 inch, a pitch of 0.193 inch, a wire diameter of 0.002 inch, and a spacing between the eight filar segments of 25% of the wire diameter. These dimensions are representative and can vary depending upon different needs. Importantly, all of the various coil shapes can be formed of the radiopaque metals listed herein so that the radiopaque inner coil 44 is radiopaque and easily seen by the physician under fluoroscopy.

The embodiment in FIGS. 2-6 also includes a non-radiopaque outer coil 56 that has an inner diameter 58 that is greater than an outer diameter 60 of the radiopaque inner coil 44 and greater than the outer diameter of the elongated core member 32. The non-radiopaque outer coil 56 is formed from a non-radiopaque material including stainless steel (SS), cobalt-chromium (CoCr), and nickel-titanium (NiTi) alloys. The non-radiopaque outer coil can range in length from 10 cm to 60 cm from a distal end 62 to a proximal end 64. In one embodiment, the non-radiopaque outer coil 56 is 30 cm long.

Figure 2:
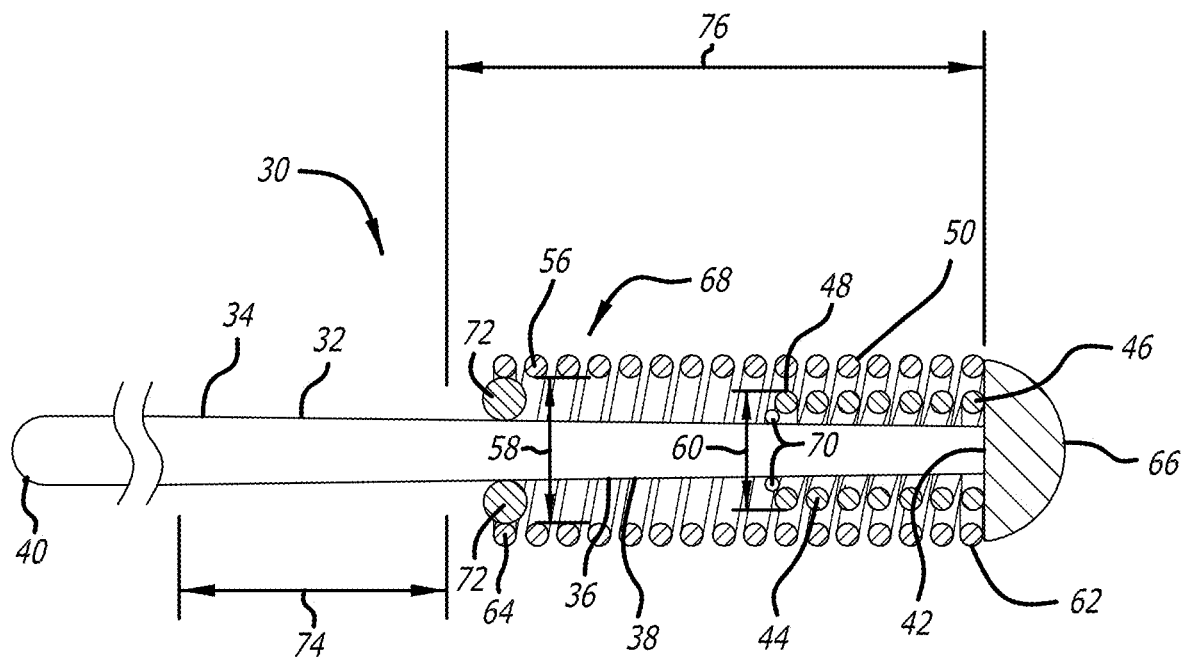
FIG. 2 is an elevational view of a guidewire of the invention depicting an inner coil and an outer coil at the distal end of the guidewire.
Figure 3:
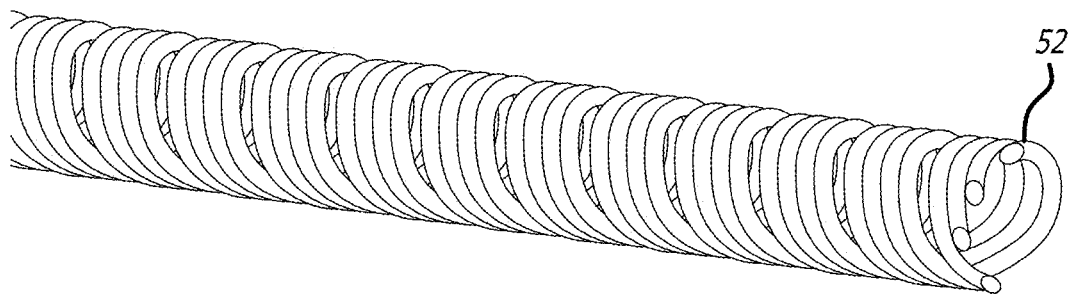
FIG. 3 is an elevational view of a multifilar guidewire for use as an inner coil or an outer coil on a guidewire.
Figure 4A:
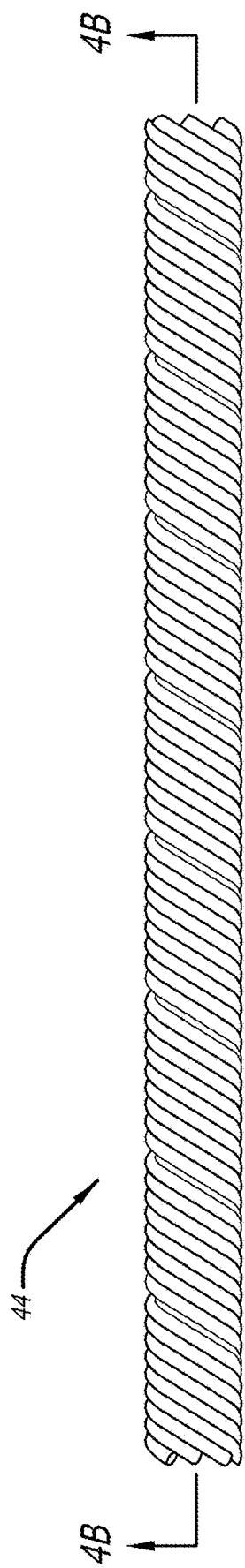
FIG. 4A is an elevational view of an eight filar strand coil for use as an inner or outer coil on the distal end of the guidewire.
Figure 4B:
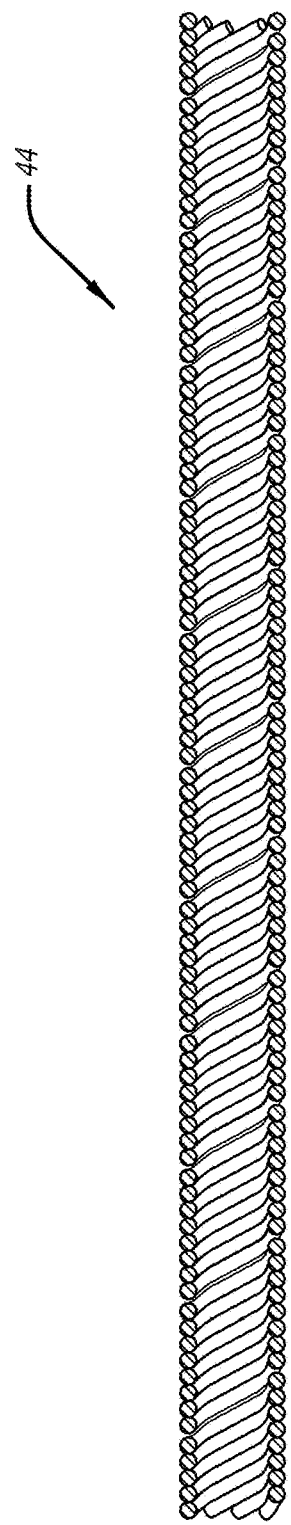
FIG. 4B is a longitudinal cross-sectional view of the eight filar strand coil of FIG. 4A.

As shown most clearly in FIG. 2, the distal end 46 of the radiopaque inner coil 44, the distal end 42 of the guidewire 30, and the distal end 62 of the non-radiopaque outer coil 56 all are connected together by solder, glue, weld or braze. Preferably, a solder ball 66 is formed at the distal end 42 of the guidewire 30 in a known manner to connect the radiopaque inner coil 44 to the non-radiopaque outer coil 56 and to the guidewire distal end 42. It is important to emphasize that the distal end 46 of the radiopaque inner coil 44 preferably does not contact the distal end 62 of the non-radiopaque outer coil 56, they are connected together by the solder ball 66, but after the solder ball 66 is formed, there may be direct contact with each other. The distal end 46 of the radiopaque inner coil 44 does contact the distal end 42 of the elongated core member 32. The proximal end 48 of the radiopaque inner coil 44 is connected to the elongated core member 32 by first solder joint 70, weld, glue, or braze, in a known manner. The proximal end 48 of the radiopaque inner coil 44 is not attached to the non-radiopaque outer coil 56. The proximal end 64 of the non-radiopaque outer coil 56 is attached to the elongated core member 32 by second solder joint 72, weld, glue, or braze, in a known manner. The first solder joint 70 is proximal of the solder ball 66 and distal of the second solder joint 72. The proximal end 64 of the non-radiopaque outer coil 56 is not connected to any portion of the radiopaque inner coil 44, thereby providing a seamless outer surface 68 along non-radiopaque outer coil 56 with no solder joint with the radiopaque inner coil to create a stiffness problem. Preferably, as shown in FIG. 2, there is a gap between the elongated core member 32 and the inner coil 44 and the outer coil 56, and a gap between the inner coil 44 and the outer coil 56. Like the radiopaque inner coil 44, the non-radiopaque outer coil 56 can be formed from the single filar coil 50, a four filar coil 56 (FIG. 3), or any number of filar coils such as the eight filar coil shown in FIGS. 4A and 4B.

Figure 5:
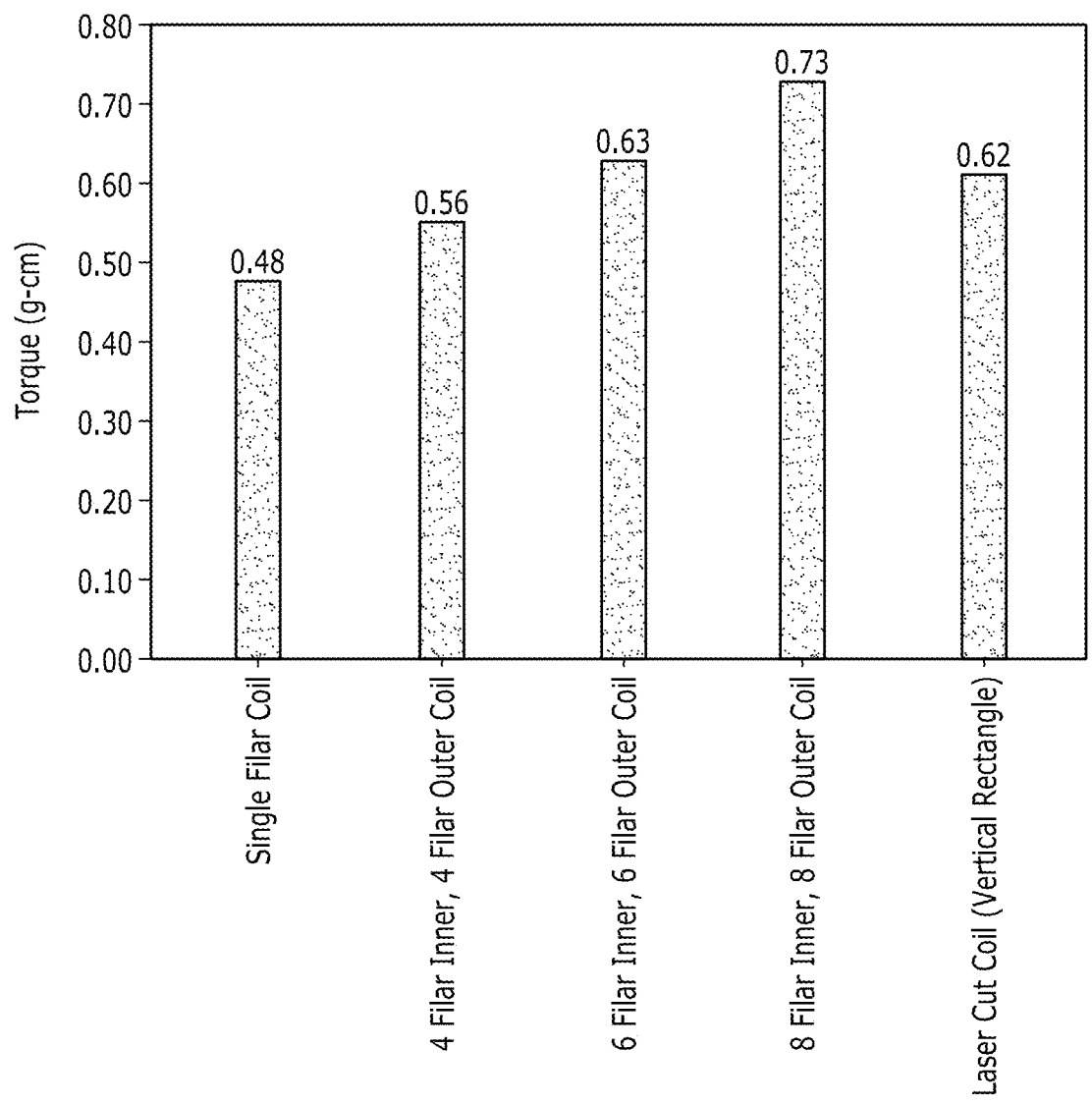
FIG. 5 is a chart depicting the torque analysis for guidewires of the invention having different filar strand coils.
Figure 8A:
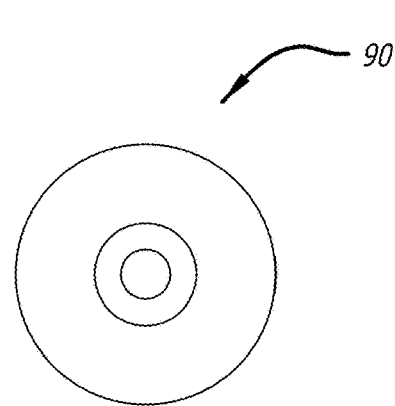
FIG. 8A is an elevational view of a mold for forming a solder joint on the distal end of a guidewire.
Figure 8B:
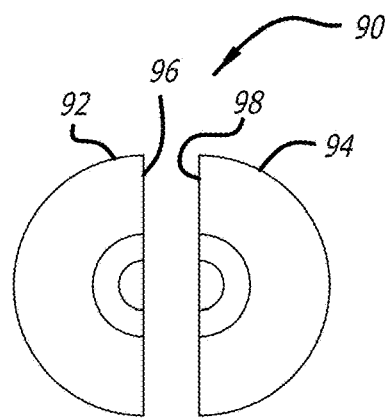
FIG. 8B is an elevational view of the split mold of FIG. 8A.

As shown in the graph in FIG. 5, experiments were conducted to determine the effects of multifilar coils on torque. In FIG. 5, the Straight Torque was measured for a guidewire having an inner and outer coil with only one filar, a guidewire having an inner and outer coil with four filars, six filars, eight filars, and an inner and outer coil that is laser cut in the form of a vertical rectangle. As can be seen in FIG. 5, the single filar coils and multifilar coils of the invention compare favorably in torque performance.

Testing also was conducted on guidewires of the invention to measure radiopacity, as seen in FIG. 6. The guidewires in Groups 1-6 have a radiopaque inner coil and a non-radiopaque outer coil, as disclosed in FIG. 2. The radiopacity of the radiopaque inner coil compares favorably under fluoroscopy compared to the commercially available WHISPER® guidewire sold by Abbott Cardiovascular Systems, Santa Clara, Calif.

In one embodiment, shown in FIG. 2, a proximal section 74 of the guidewire 30 has a silicone based hydrophobic coating and a polytetrafluoroethylene coating (PTFE). A distal section 76 has a polyvinylpyrrolidone hydrocoat coating (PVP). Typically, the distal end 42 of the guidewire 30 is uncoated.

Mold for Forming Solder Distal Tip

Guidewires are available in many different configurations including tip load, support profile, and materials of construction, all selected by a physician for specific clinical case requirements. For certain situations it has been perceived that a guidewire distal tip with a specific geometry provides the physician a mechanical advantage in navigating a tortuous path or occluded segment. In this embodiment, the characteristics of molten solder flow is overcome to contain the molten solder flow within a predetermined shape. Currently, a solder joint is formed at the distal tip of the guidewire attaching the elongated core wire to the outer coils. This solder joint is formed utilizing a conventional soldering iron to heat and flow the solder onto the core wire and secure the coils to the core wire when solidified. The present invention creates a soldered tip by a different means, and allows a specific shape to be achieved by casting the molten solder in a predetermined shape.

As shown in FIGS. 7A-10B, a mold 80 is used to cast the soldered tip, which overcomes many obstacles both in cost and manufacturability. Using the mold 80 to form a predetermined soldered shape provides not only the intended geometry of the solder joint, but also performs the necessary solder bond attaching the guidewire elongated core wire to the outer coils (see FIGS. 2-6 for example). The mold could be machined as simple as a bullet shaped tip 82 or it could be machined to include a small angular feature to what is referred to as a micro-J shaped tip 84. Utilizing mold 80 to perform this solder tip operation allows the engineering team the ability to change the configuration to suit the requirements for the product being produced.

The mold 80 is made as a solid mold constructed of ceramic or other suitable material able to withstand the temperature required to receive molten solder. The mold 80 has a cavity 86 which receives the molten solder and the distal tip of the guidewire elongated core wire, and the distal end of any coils, if present. The shape of the cavity 86 determines the shape of the solder joint, such as the bullet shaped tip 82 and the micro-J shaped tip 84.

A more complex shape is achieved by utilizing a split mold 90 where a first shell 92 and a second shell 94 are held together while the solder is molten, and then separated to release the solder tip 88. The split mold 90 has the solder tip 88 configuration machined into a first face 96 and the mirror image machined into a second face 98. The split mold 90 can be machined as the bullet shaped tip 82 or to include a small angular feature to form the micro-J shaped tip 84. Various other solder tip 88 shapes can be formed by the spilt mold 90 such as cone shaped, truncated cone shaped, and a textured surface.

The method to form the solder tip 88 includes placing the molds into a heating apparatus and allowing the solder to become molten. Once molten, the distal tip of a guidewire elongated core wire is submerged into the mold cavity 86 allowing solder to flow onto the distal tip and the first few winds of the outer coil (if present). A thermally conductive material can be placed around segments of the outer coil, just above the mold cavity 86, to prevent solder from flowing to undesirable places and control the precise placement of the solder tip 88. Once the solder has flowed to the specified area, the split mold 90 is rapidly cooled allowing the solder to solidify and bond the guidewire distal tip and coils together. Once cooled, the part may be withdrawn from mold 80, or the first and second shells 92, 94 are separated, and the solder tip 88 can be removed.

Utilizing mold 80 to form the solder tip 88 allows the engineering team the ability to quickly change the configuration for the product being produced.

Figure 9A:
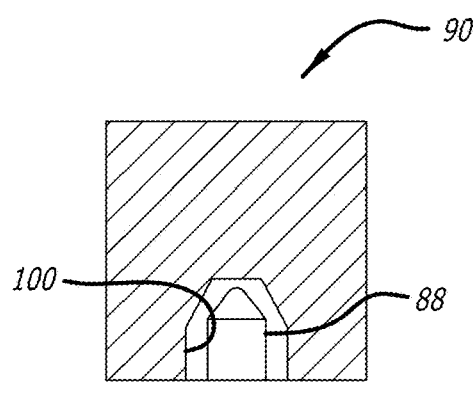
FIG. 9A is a cross-sectional view of a mold used for forming a solder joint at the distal end of a guidewire and depicting the cavity for receiving a molten metal.
Figure 9B:
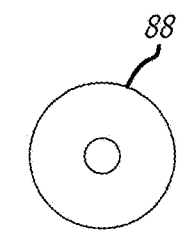
FIG. 9B is a top view of the solder joint formed by the mold of FIG. 9A.
Figure 9C:
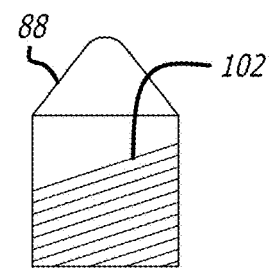
FIG. 9C is an elevational view of the solder joint formed by the mold of FIG. 9A.
Figure 10A:
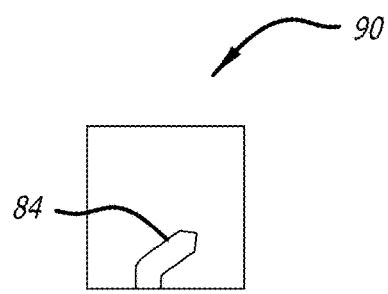
FIG. 10A is an elevational view of a mold for forming a solder joint having a micro-J shape.
Figure 10B:
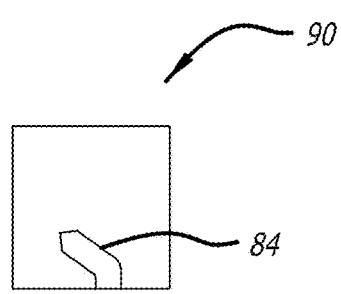
FIG. 10B is an elevational view of a mold for forming a solder joint having a micro-J shape.

Additionally, the first face 96 and the second face 98 can be modified to provide some type of feature or texture depending on the needs of the specific product driven by the application. The mold 80 may possess some form of texture or even have grooves, either raised or recessed, to allow a specific outer surface geometry as required for specified product requirements. For example, as shown in FIGS. 9A-9C, split mold 90 has angular grooves 100 formed in the mold cavity 86 so that the solder tip 88 has matching angular grooves 102.

While the vast majority of guidewires will use solder to form the bond at the distal tip and connect the coils, some guidewires may use epoxy or another similar material instead of solder. The foregoing description relating to FIGS. 7A-10B relating to the solder tip 88 applies as well to other suitable metals and epoxy.

Laser to Form Dimpled Joint

Figure 11A:
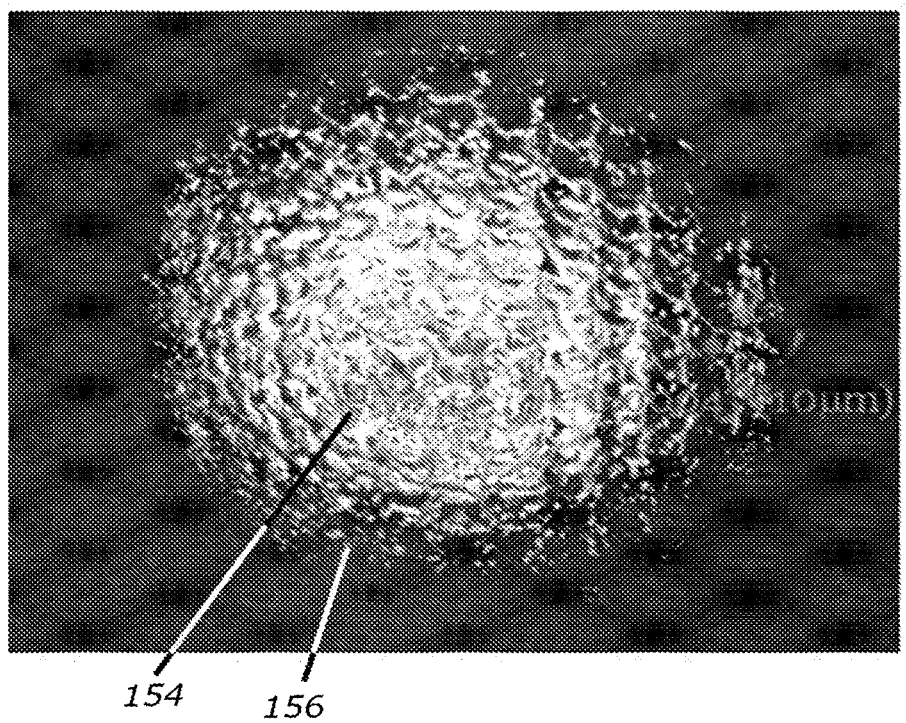
FIG. 11A is a top view of a joint depicting a series of dimples formed by a laser.
Figure 11B:
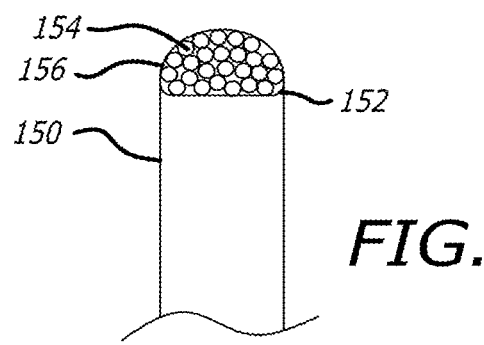
FIG. 11B is an elevational view of the joint of FIG. 11A.
Figure 12A:
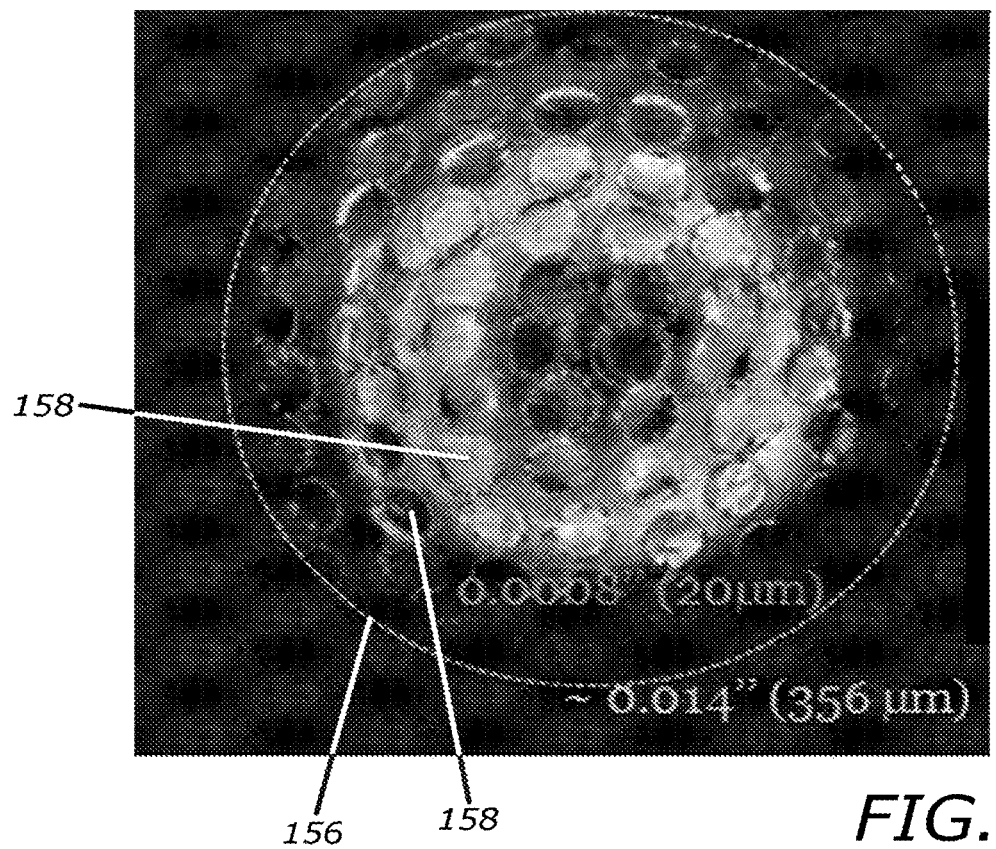
FIG. 12A is a top view of a joint depicting a series of dimples formed by laser.
Figure 12B:
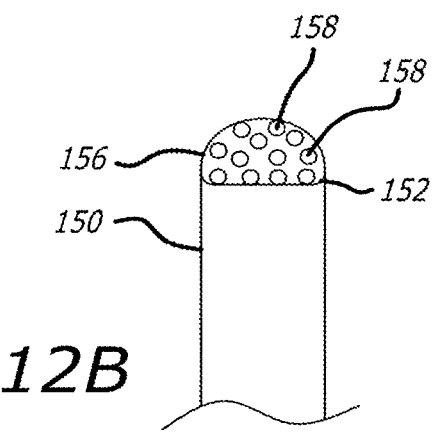
FIG. 12B is an elevational view of the joint of FIG. 12A.
Figure 12C:
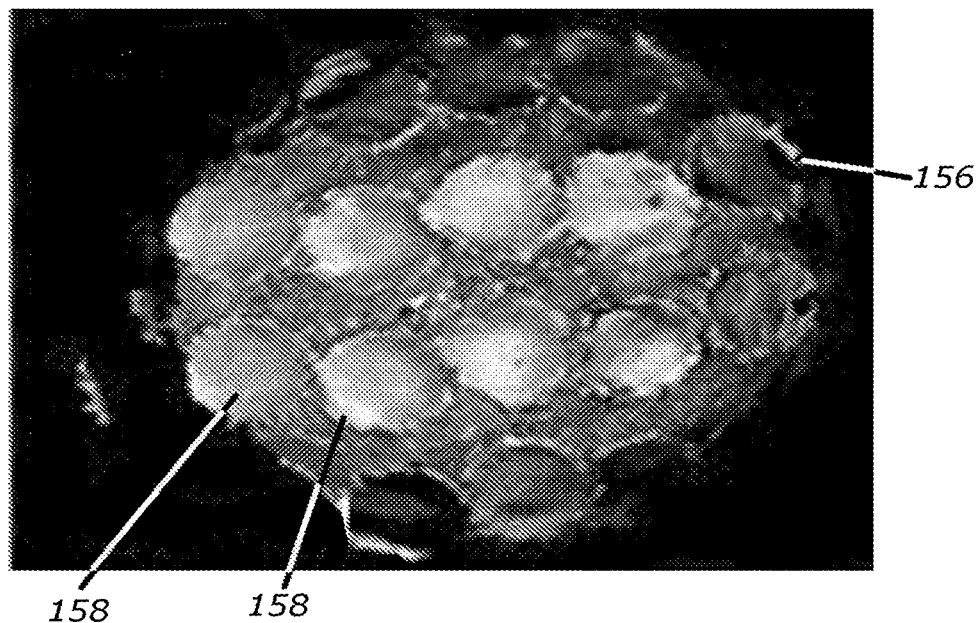
FIG. 12C is an enlarged top view of the joint of FIG. 12A.

Generally, most commercially available guidewires have guidewire tips made from solder material or weld material and have a smooth, dome-shaped surface. Such guidewires encounter challenges when used to cross calcified and fibrous tissues, to treat chronic total occlusions (CTO). Certain commercially available guidewires are designed to have higher tip loads in order to treat CTO and penetrate through complex and stenosed lesions. Optimal wire strength, tip load and tip shape help with push-ability and maneuvering the guidewire through the lesions, however, with a smooth tip surface likely will have challenges engaging calcified and fibrous tissues resulting tip deflection and failure to penetrate through the lesion. In one embodiment, shown in FIGS. 11A-12D, a laser (not shown) is used to form a textured or roughened surface 154 on the solder/weld joint 156 at the distal tip of the guidewire 150. Commercial lasers, such as a fiber laser, are capable of a focused spot of approximately 0.001 inch, and can provide random or tightly stitched patterns as shown in FIGS. 11A and 11B, or provide spaced apart dimples 158 as shown in FIGS. 12A-12C. The dimples 158 resemble the dimples on a golf ball and can have specific spacing and patterns. In one embodiment, the laser creates a series of dimples 158 that have a diameter of 0.001 inch and are spaced apart 0.001 inch. In another embodiment, the dimples 158 have a diameter in the range from 0.0005 inch to 0.005 inch and have spacing between dimples 158 in the range from 0.0005 inch to 0.005 inch. In another embodiment, the laser creates dimples 158 having a diameter of 0.001 inch and spaced apart by 0.0005 inch, which forms the textured surface 154. It is also possible to provide greater spacing between the dimples 158 to provide a mechanical advantage in specific clinical cases. The laser can be programmed to provide areas on the solder/weld joint 156 that are left untouched (i.e., smooth), depending on the application. The ablated patterns (dimples 158) are easily modified by simply altering the laser frequency, grid spacing (spaced apart dimples 158), or programming dimple by dimple to achieve an optimal configuration.

Figure 12D:
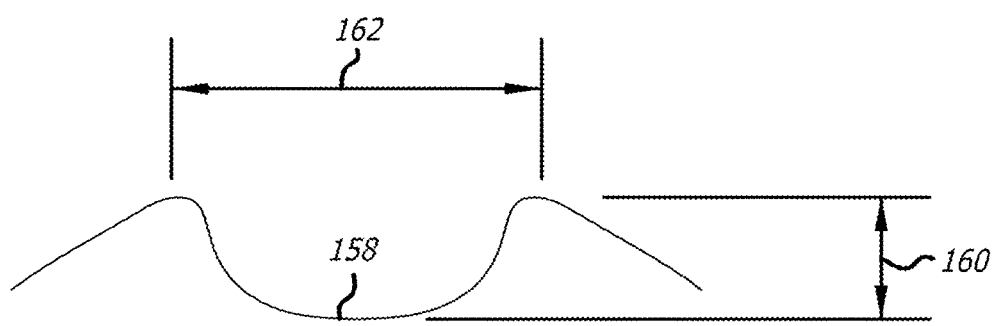
FIG. 12D is a side view depicting one dimple formed in the joint depicted in FIG. 12C.

The dimples 158 also have a depth dimension 160 and a diameter 162 as shown in FIG. 12D. Preferably, the dimples 158 have a depth dimension 160 ranging from 0.5µ to 1.5µ, and more preferably 1.0µ.

Similarly, the radius dimension 162 of dimples 158 can range from 0.3µ to 6.0µ, and preferably from 2.0µ to 4.0µ, and more preferably 3.0µ. The process involves utilizing a commercially available fiber laser, with the wire tip fixture end on, to selectively soften and dimple the solder/weld surface of the guidewire tip where the beam is directed. This process is performed without disrupting the solder/weld structural integrity of the solder or weld material due to the extremely fast pulse rate of the laser providing focused heating only where the beam is targeted. In one embodiment, the cycle time for the laser process is 50 ms, which allows for a modified tip texture in a time that is acceptable in a production environment. Higher or lower laser cycle times are acceptable depending on the composition of the solder/weld and the size and depth of the dimples.

In addition to using a commercially available laser, the dimples 158 can be formed by other processes including bead blasting, chemical etching, or mechanical impact, as long as the integrity of the solder/weld joint 156 is maintained.

The dimples 158 can be formed on the solder/weld joint 156 after the joint has been formed on the distal tip 152 of the guidewire 150. Alternatively, the solder/weld joint 156 is manufactured at a component level and the dimples 158 are then formed on the joint. Thereafter, the solder/weld joint 156 with the pre-formed dimples 158 can be attached to the distal tip 152 of the guidewire 150.

Figure 12E:
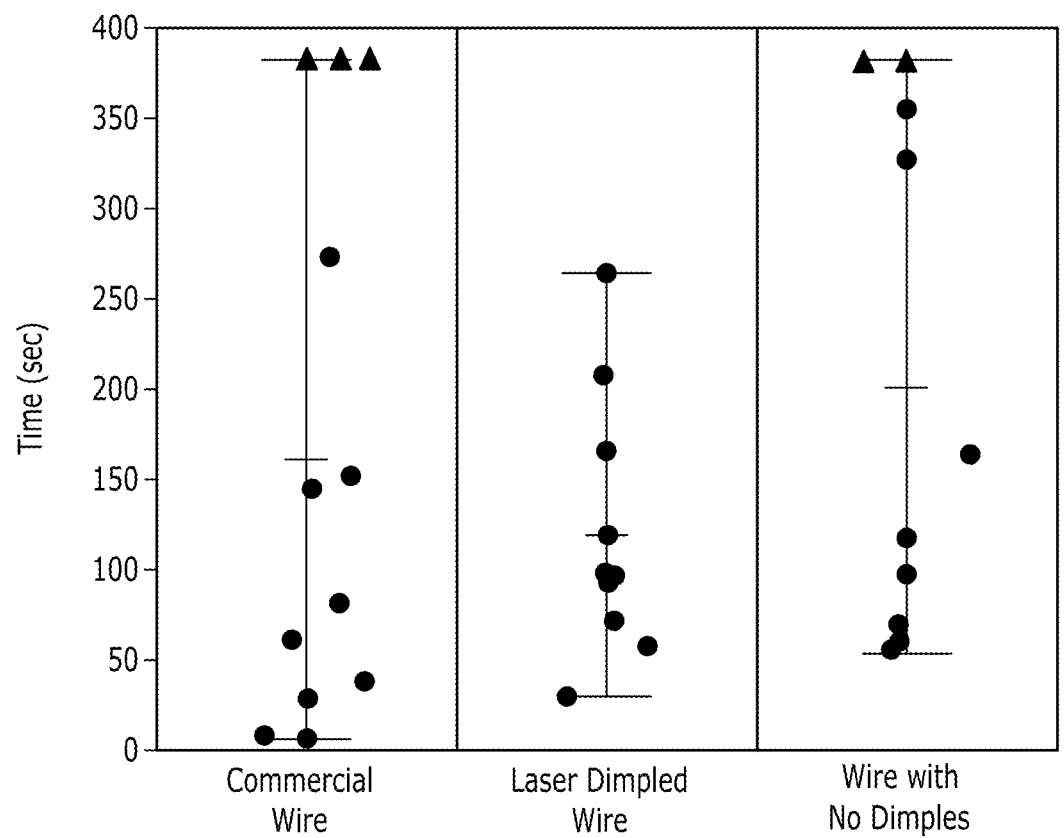
FIG. 12E is a chart depicting test data comparing the time to pass through a lesion for the laser dimpled guidewire compared to a commercially available guidewire.

As shown in FIG. 12E, an experiment was conducted comparing lesion crossing performance of the laser dimpled guidewire with commercially available guidewires. Testing was performed on a clinically relevant Chronic Total Occlusion (CTO) model to determine the time to pass the guidewire through the lesion. The round dots represent the time in seconds it took the guidewire to pass through the lesion, while the triangular dots represent those guidewires that were unable to pass through the lesion. As can be seen in FIG. 12E, the laser dimpled guidewire performed substantially better than a commercially available guidewire and a wire with no dimples in terms of consistently better passing times, and no failed attempts to pass through the lesion.

Coils with Different Cross Section Shapes

Generally, the distal end of a guidewire should have a low support profile to make it flexible enough for cross-ability purposes. Therefore, the distal end of the core wire is ground (tapered) and covered with a coil to make it flexible and atraumatic (see e.g., FIGS. 2-3). Also, the coil will assist with keeping the outer diameter of the guidewire consistent. Prior art coils are formed from a wire with a circular cross section (FIG. 13) and cut with a laser.

For the next generation guidewires, good torque response without negatively affecting the bending stiffness of the guidewire is an important functional attribute.

In the present invention, multiple wire cross-sections were designed to improve the functionality of the guidewires. Finite Element Analysis (FEA using ABAQUS commercial software) was performed on these guidewire cross sections to identify the effect of different cross-sections on torque response and bending stiffness.

Figures 13, 14:
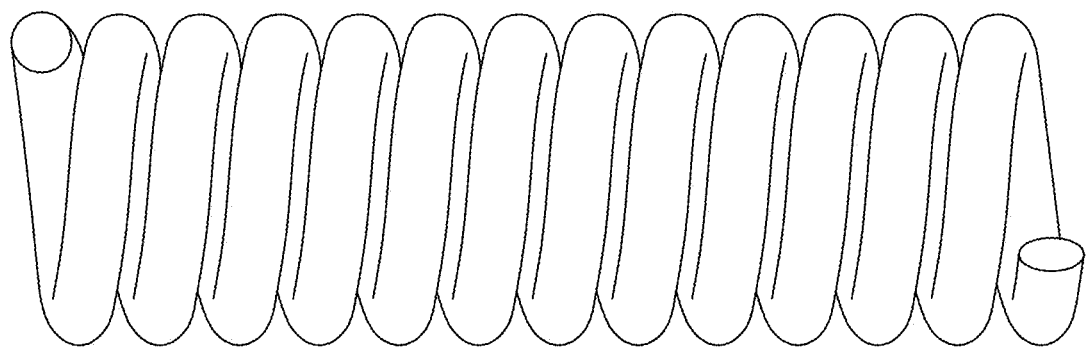
FIG. 13 is an elevational view of a prior art coil having a circular or round cross-section wire.
FIG. 14 is a chart depicting the elastic modulus, yield strength, and ultimate strength of 304V stainless steel.
Figure 18A:
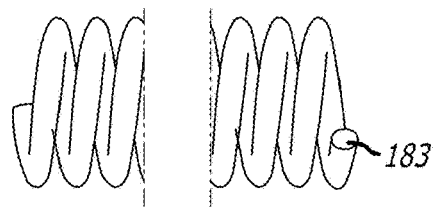
FIGS. 18A and 18B are elevational and front views respectively, of a coil having a vertical ellipse cross-section.
Figure 19A:
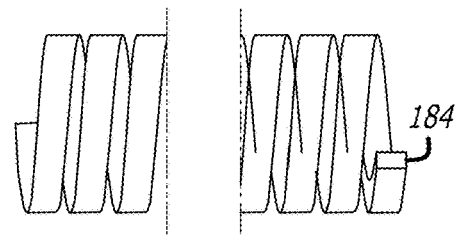
FIGS. 19A and 19B are elevational and front views respectively, of a coil having a square cross-section.
Figure 18B:
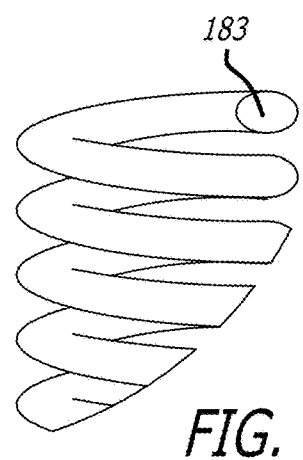
Figure 19B:
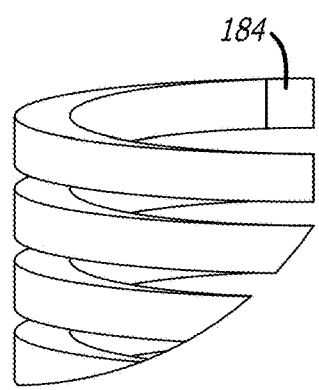
Figure 20A:
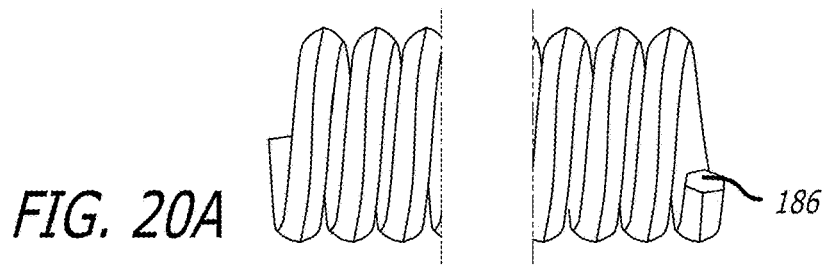
FIGS. 20A and 20B are elevational and front views respectively, of a coil having a vertical hexagonal configuration.
Figure 20B:
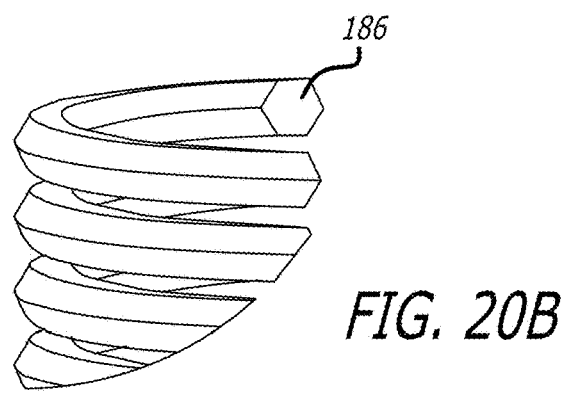
Figure 21A:
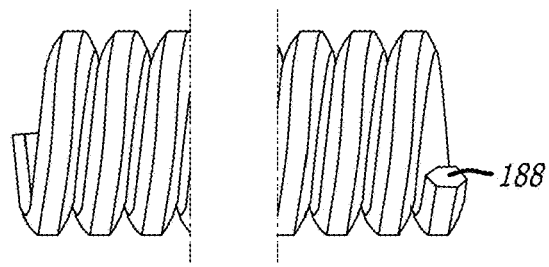
FIGS. 21A and 21B are elevational and front views respectively, of a coil having a horizontal hexagonal cross-section.
Figure 22A:
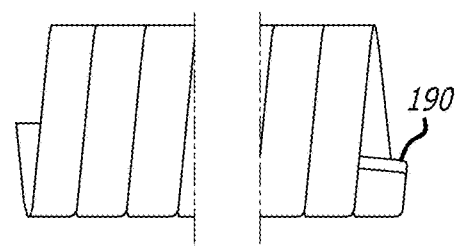
FIGS. 22A and 22B are elevational and front views respectively, of a coil having a flat cross-section.
Figure 21B:
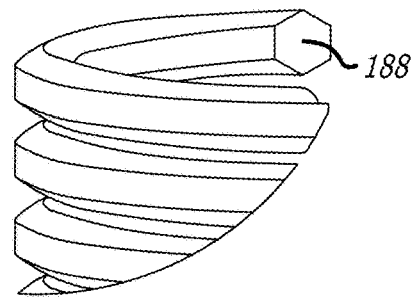
Figure 22B:
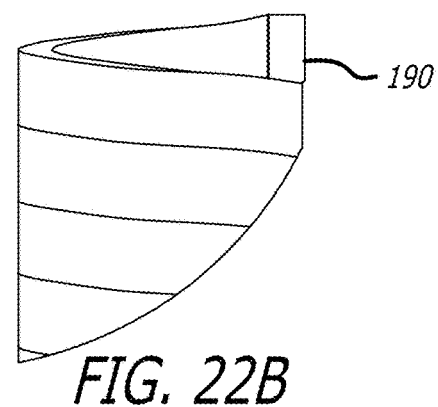
Figure 23A:
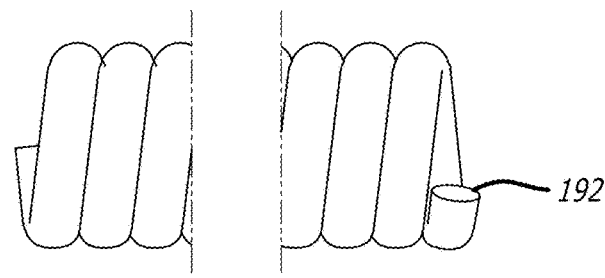
FIGS. 23A and 23B are elevational and front views respectively, of a coil having a horizontal elliptical cross-section.
Figure 23B:
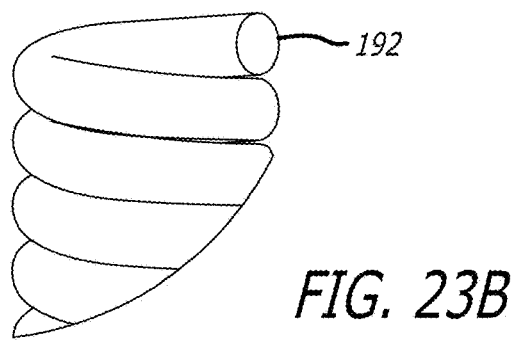

The present invention increases the torquability without negatively affecting the bending stiffness and functionality of guidewire using different cross-section shapes of coils. As shown in FIGS. 15A-23B, the different embodiments include circle 178 (prior art), I-beam 180, vertical rectangular 182, vertical ellipse 183, square 184, vertical hexagonal 186, horizontal hexagonal 188, flat 190, and horizontal ellipse 192 cross-sections. FEA demonstrates that the more material removed away from the Neutral Axis (N. A.) of the coil wire, increases the torquability while decreasing the bending stiffness. Coils with different cross-sections were created and subjected to torque while keeping the other parameters such as material and volume of the coil wires constant. For this study, the coil material considered was 304V stainless steel. FIG. 14 shows the material properties for 304V stainless steel. In order to keep the volume constant, the cross-sectional area, the length, the nominal diameter, and the pitch for the wires were kept constant.

Figure 24:
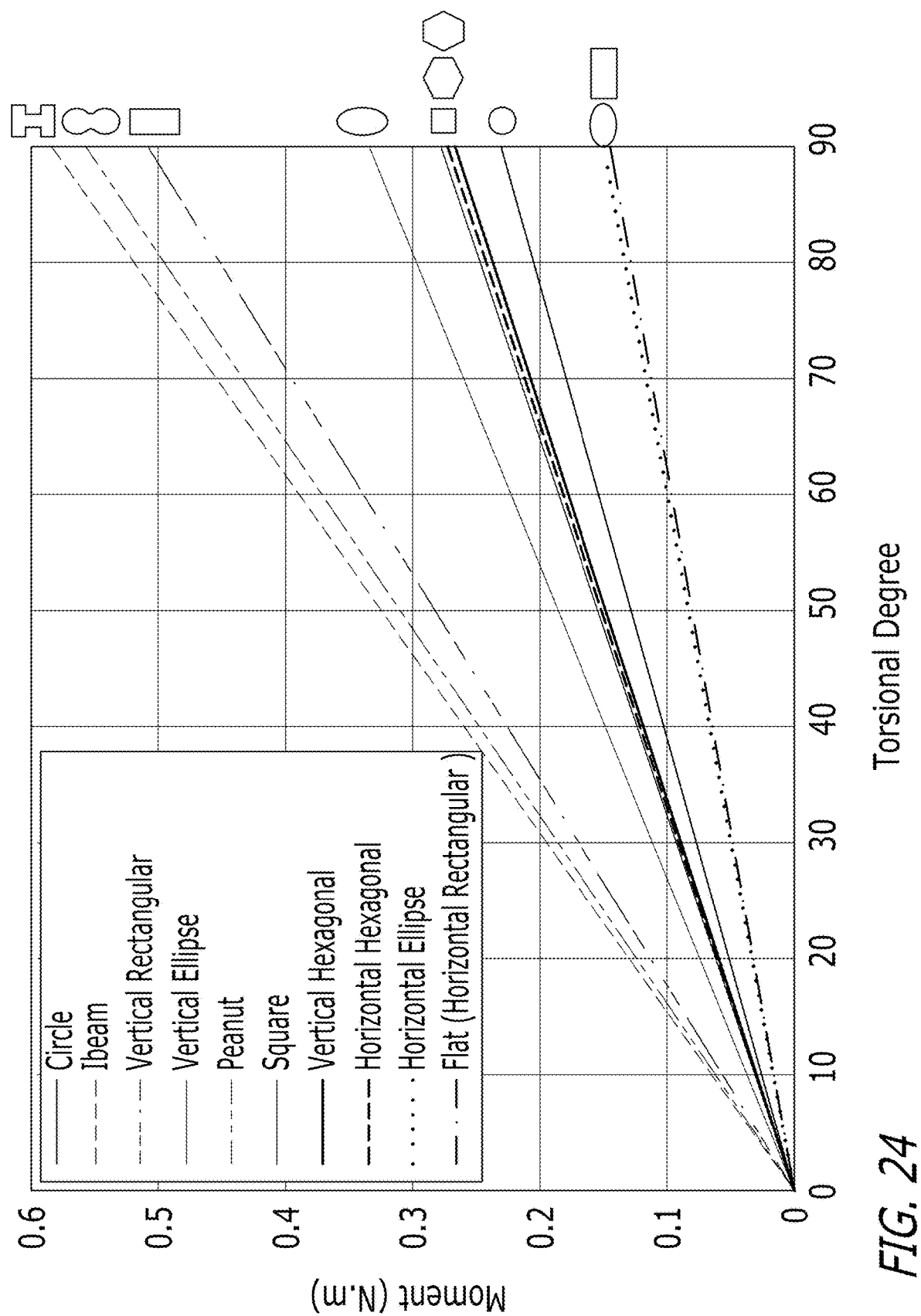
FIG. 24 depicts the torque response of single wire coils having different cross-sections shown in FIGS. 15A-23B.
Figure 25:
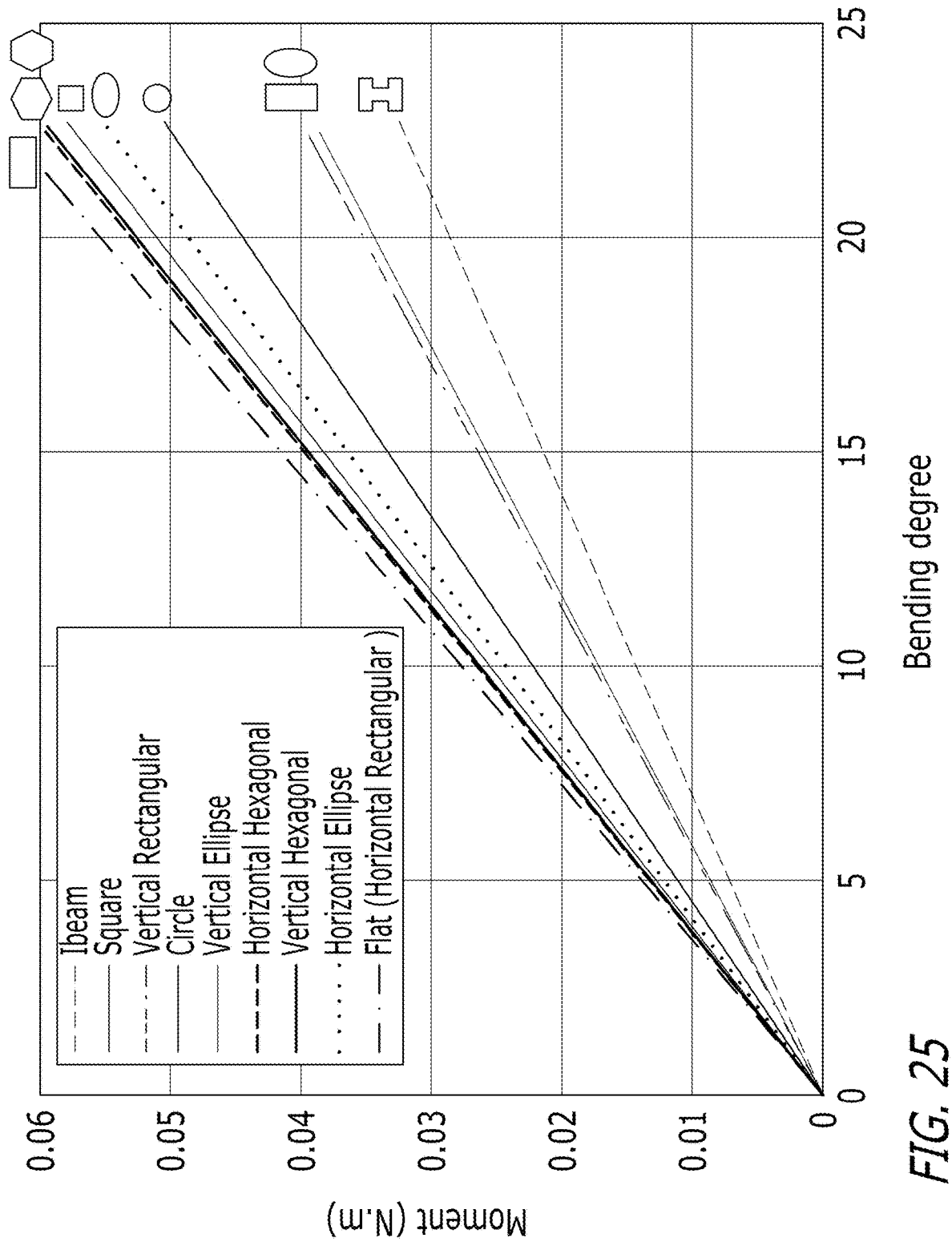
FIG. 25 is a chart showing the bending stiffness of the coils having different cross-sections as depicted in FIGS. 15A-23B.
Figure 26:
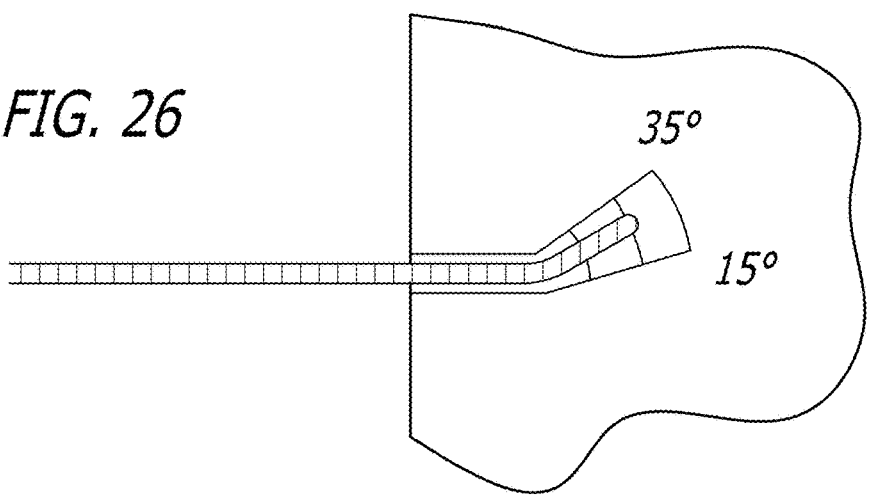
FIG. 26 is an elevational view of a distal end of a guidewire inserted into a fixture depicting the angular shape of the micro-J bend in the distal tip of the guidewire.
Figure 27A:
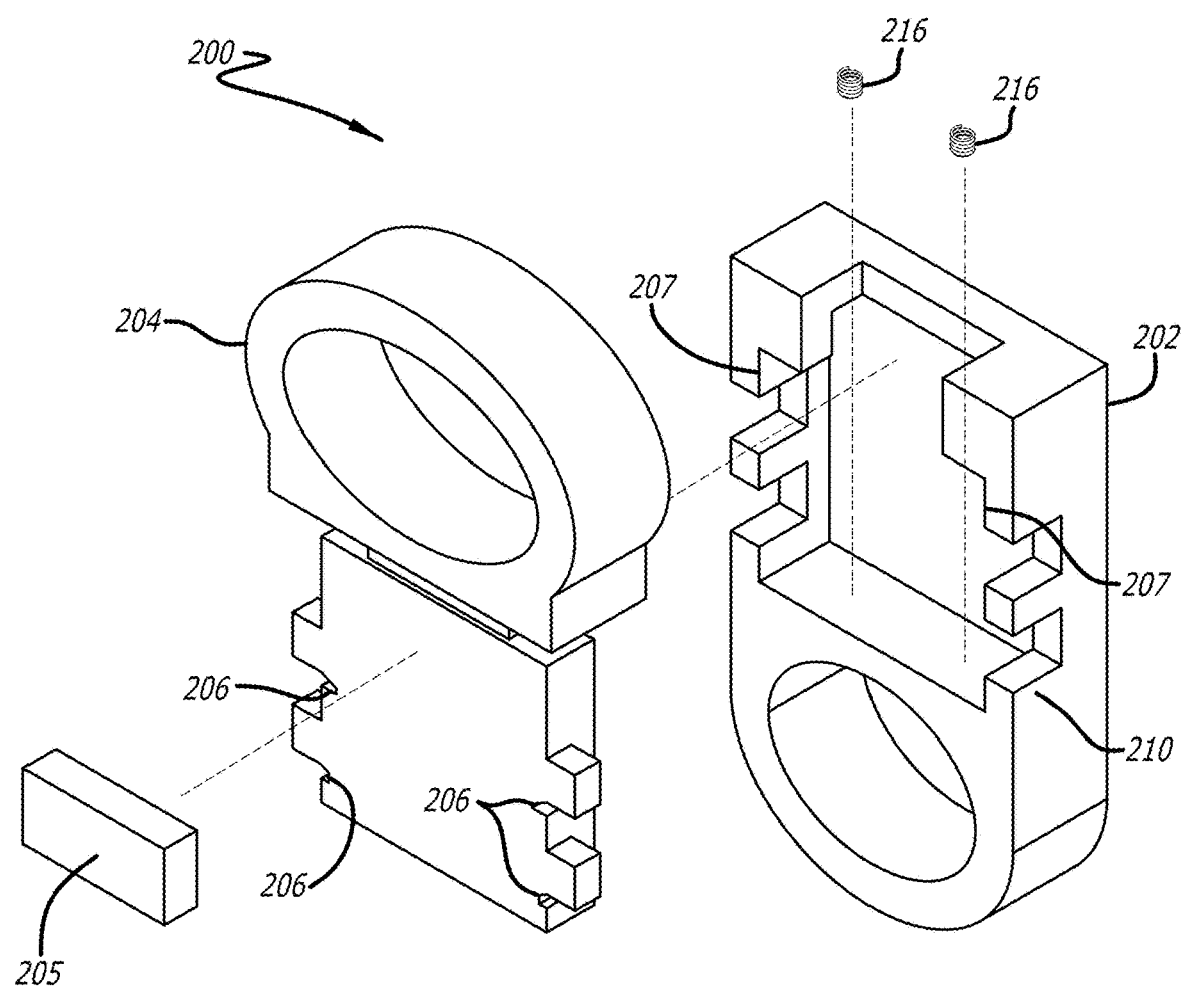
FIG. 27A is an exploded perspective view of a shaping tool for forming a micro-J bend in the distal end of a guidewire.
Figure 27B:
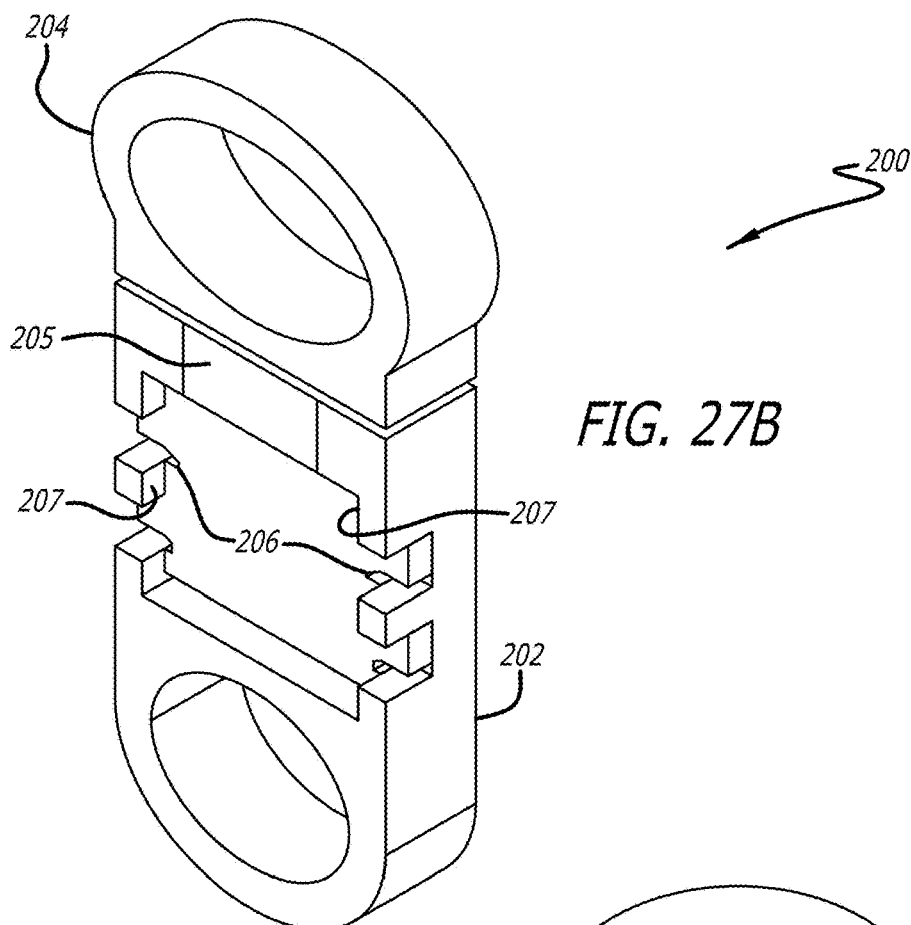
FIG. 27B is an elevational perspective view of a shaping tool for forming a micro-J bend in the distal end of a guidewire.
Figure 28A:
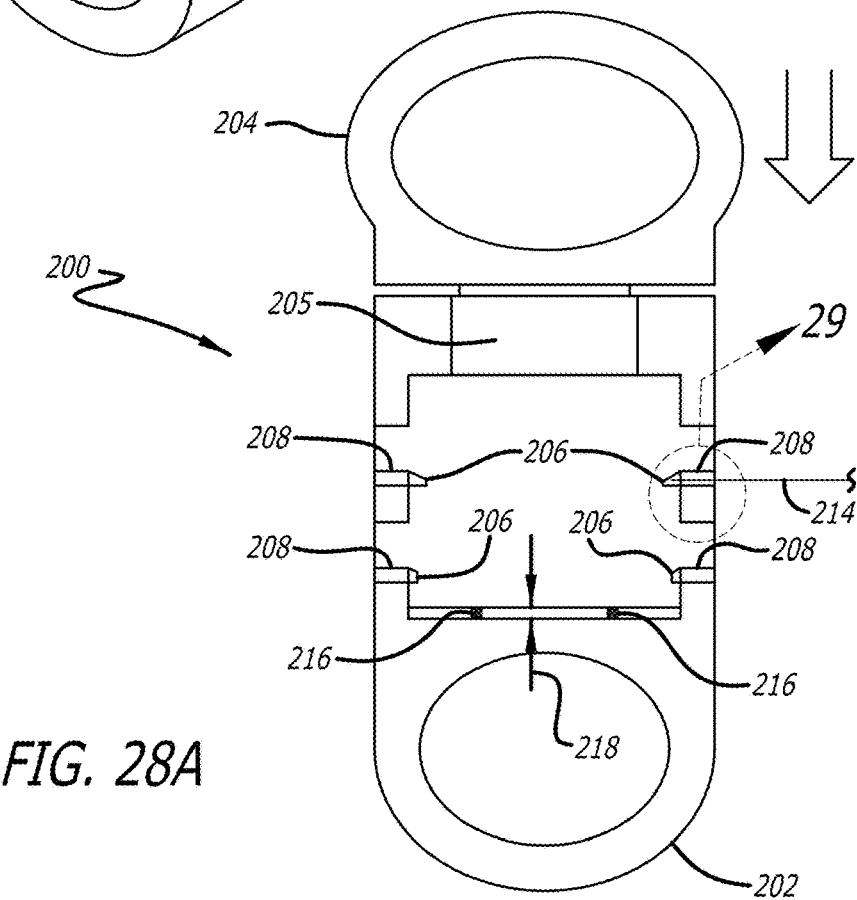
FIG. 28A is an elevational view of a shaping tool in an open position for forming a micro-J bend in the distal end of a guidewire.
Figure 28B:
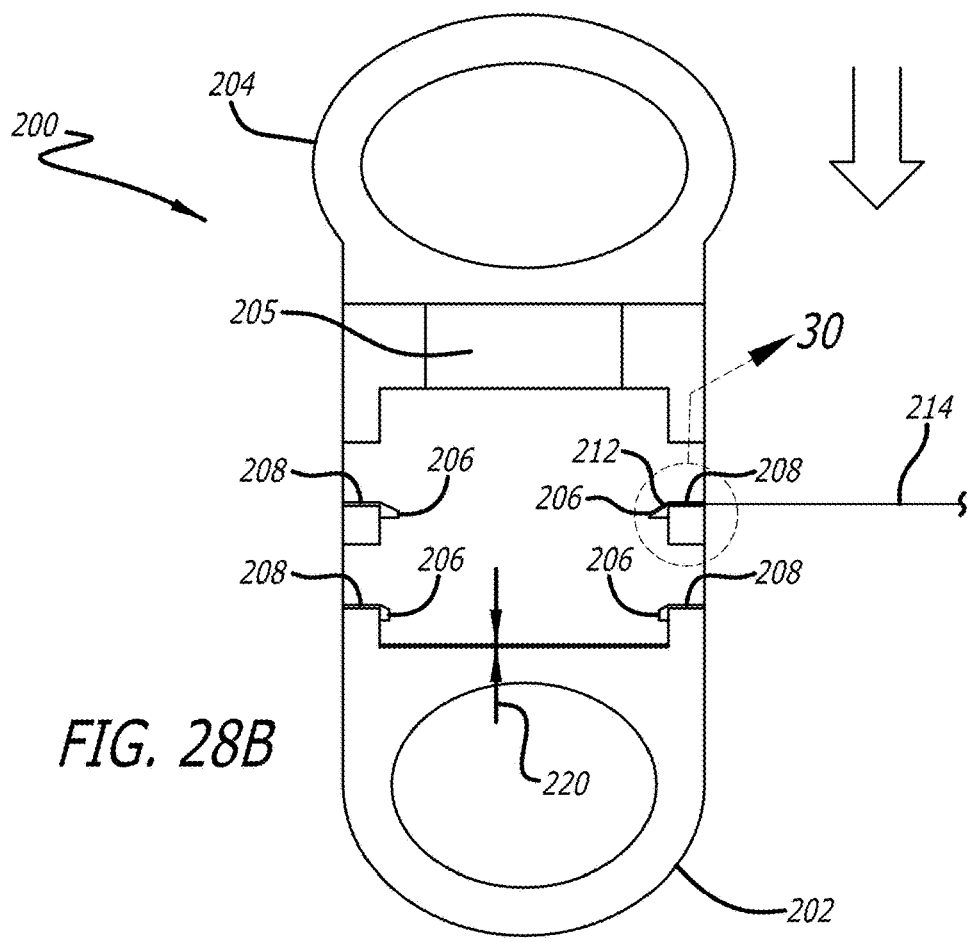
FIG. 28B is an elevational view of a shaping tool in a closed position forming a micro-J bend in the distal end of the guidewire.
Figure 29:
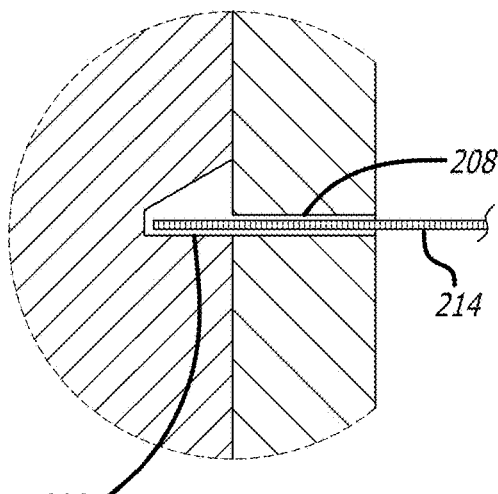
FIG. 29 is an enlarged circular view taken along lines 29-29 depicting a channel and a cavity for receiving the distal end of a guidewire.
Figure 30:
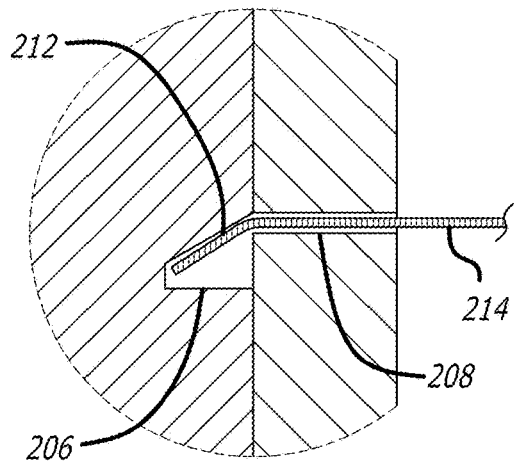
FIG. 30 is an enlarged circular view of the cavity of FIG. 29 in which a guidewire has been inserted through the channel and in to the cavity and is being bent into a micro-J shape.

Coils having different cross sections with the same length, pitch, mean diameter and cross-sectional area (dimensions scaled up to 100) are shown in FIGS. 15A-23B. FIG. 24 shows the torque response of single coils with different cross-sections analyzed by ABAQUS using the provided material properties. The torsional stiffness of the I-beam is the highest followed by the rectangular and vertical ellipse cross-sections. A peanut shaped cross-section wire also showed high torsional stiffness (FIG. 24). FIG. 25 shows the bending stiffness of the coils with different cross-sections. Therefore, by changing the cross-section of the wire of a coil from circular to I-beam, the torque response increased up to 250% while decreasing the bending stiffness by 50%. Considering the constraints due to manufacturing, dimensions and tolerances the I-beam, peanut, vertical rectangular and vertical ellipse shapes are more favorable than the conventional round cross-section coils, depending on the application or other limitations.

In FIGS. 15A-23B, the shapes and sizes related to the coils 178, 180, 182, 183, 184, 186, 188, 190 and 192 are for illustrative purposes and to ensure the parameters such as length, pitch, mean diameter and cross-sectional area of the coil wires were constant for testing purposes.

The coils 180, 182, 183, 184, 186, 188, 190 and 192 can be used with the guidewire 30 shown in FIGS. 2-6 and can be used as either an inner coil or an outer coil.

Guidewire Tip Shaping Tool—Micro J

Guidewires are sold either in a straight or pre-formed "J" shaped configuration. Generally, the distal tip of the guidewires are micro "J" shaped to assist with maneuverability. Wires can be shaped by the manufacturer or by the physician using a shaping tool provided with the guidewire. Shaping by the manufacturer is an automated process, which is more repeatable and does not compromise the integrity of the wire. The majority of users prefer a straight wire and shape the tips themselves. Guidewire manufactures provide a mandrel and introducer to assist physicians with the wire shaping.

It has been determined that users do not have good control in how they shape the wire and can easily damage the wire. Testing shows that there is an optimal angle (i.e., ~20°-30°) and distance from the tip (2-3 mm) that can significantly help with the wire performance. Even though physicians know what specifications they want in the bend, due to the size, most of the physicians are nowhere close to the intended optimal dimensions. Also, there is a higher risk of the wire losing integrity and functional performance if the physician performs the shaping.

In this embodiment, shown in FIGS. 26-30, a micro "J" shaping tool can be shipped with the guidewires or can be sold as a standalone accessory. This shaping tool will have pre-defined existing slots where a physician can decide the angle as well as the distance from the tip to form the micro-J bend. This tool has a universal design and will be compatible with all manufacturers guidewires as well.

In this embodiment, shown in FIGS. 27A-30, a shaping tool 200 includes a first member 202 and a second member 204, and multiple cavities 206 having different depths and shapes. A channel 208 extends through a wall 210 of the first member 202 and provides access for the distal end 212 of the guidewire 214. The second member 204 is slidably contained in the first member 202 and a third member 205 is inserted into a slot 207 in the first member 202 to hold the second member 204 in the first member 204. The third member 205 can be glued or laser welded in the slot 207, but it allows for longitudinal movement or sliding between the first member 202 and the second member 204. A pair of springs 216 are spring biased to keep the spacing tool 200 in an open position 218. In the open position 218, the distal end 212 of the guidewire 214 can be inserted through channel 208 and advanced into one of the cavities 206 (see FIG. 27B). To form the micro-J tip, the user pushes the end of the second member 204 in the direction of the arrow in FIGS. 28A and 28B, which overcomers the spring force of springs 216. As shown in FIGS. 28A-30, the second member 204 slides relative to the first member 202 to closed position 220. In the closed position 220, the cavities 206 have shifted relative to the channels 208 so that the guidewire distal end 212 will bend the predetermined angle and the bend will be set at a predetermined length from an end 222 of the distal end 212. When the user releases pressure on the end of the shaping tool 200, the springs 216 spring open and move the first member 202 to the open position 218 so that the guidewire 214 can be removed from the cavity 206. While the cavities 206 depict angular bends of 25° and 30°, a range of angular bends from 5° to 40° is contemplated. Similarly, the length of the bend from the distal end 220 to the unbent portion of the guidewire 214 is preferably 1 mm or 2 mm, however, the length can range from 0.5 mm to 5 mm.

Parabolic Grind Profile

Figure 31:
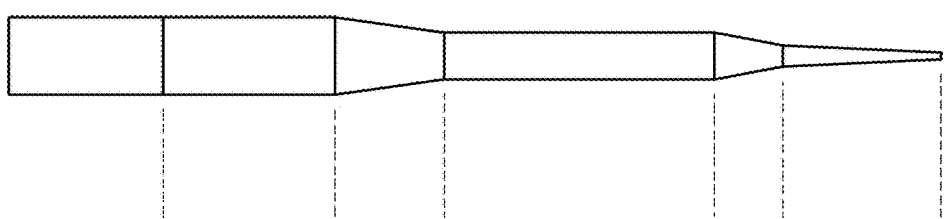
FIG. 31 is an elevational view of a prior art guidewire depicting a distal section having multiple tapered sections.

In another embodiment of the invention, the distal section of the guidewire is reduced in cross-section to be more flexible when navigating tortuous vessels, such as coronary arteries. The distal section of the guidewire must be both flexible and pushable, that is the distal section must flex and be steerable through the tortuous arteries, and also have some stiffness so that it can be pushed or advanced through the arteries without bending or kinking. A prior art guidewire is shown in FIG. 31 and has a distal section comprised of tapered sections and core sections with no taper. The resulting bending stiffness is shown in the graph in FIG. 33 wherein the bending stiffness decreases at each tapered position, and the bending stiffness remains constant along the core section that is not tapered. The tapered distal section of the prior art guidewire of FIG. 31 provides abrupt changes in bending stiffness that can reduce the tactile feel to the physician when advancing the guidewire through tortuous anatomy. In fact, in some prior art guidewires, the abrupt change in bending stiffness can result in the distal tip of the guidewire to kink or prolapse into a side branch vessel as shown schematically in FIG. 34. Prolapse can be dangerous to the patient in that the artery can be damaged or punctured. Importantly, it is preferred to maintain the outer diameter of the core section as far distal as possible to maintain torque. Each tapered section loses torque, which is critical in advancing the guidewire through tortuous vessels.

Figure 32:
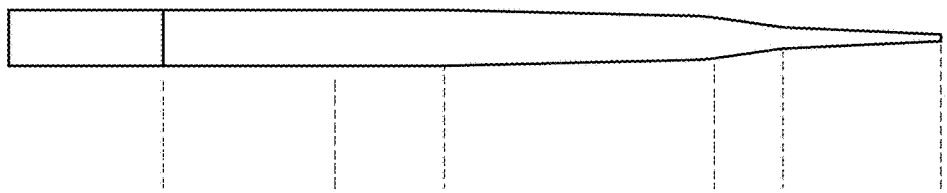
FIG. 32 is an elevational view of a guidewire depicting a distal section having a parabolic grind profile.
Figure 33:
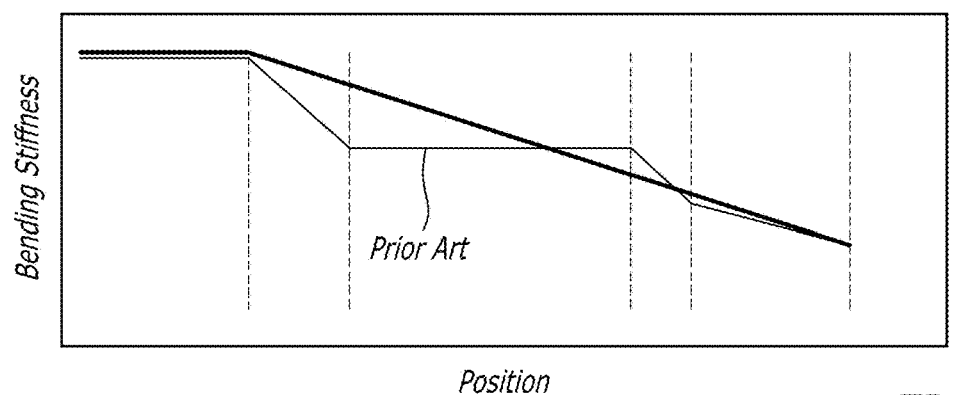
FIG. 33 is a graph depicting the bending stiffness along the distal section of the guidewires shown in FIGS. 31 and 32.
Figure 34:
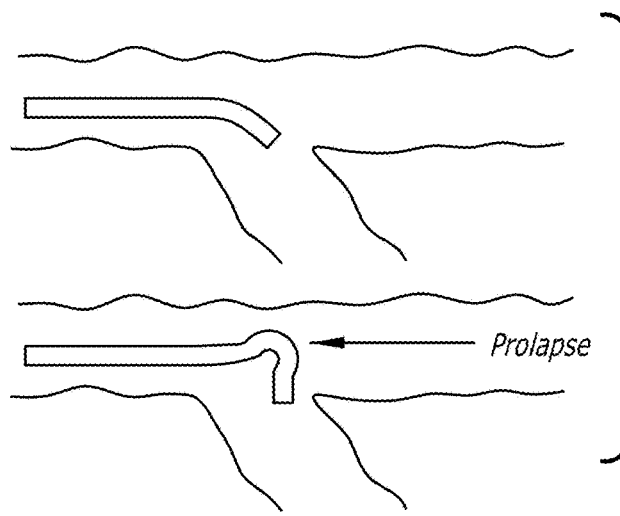
FIG. 34 is a schematic depicting the tapered distal section of a prior art guidewire kinking in a side branch vessel.

In keeping with the invention, a parabolic distal section 232 of a guidewire 230 is shown in FIG. 32 wherein a significant portion of the distal section has been ground to form a continuous taper. More specifically, the continuous taper is formed by a parabolic grind along parabolic distal section 232 of the guidewire 230. The parabolic grind provides a smooth curvilinear transition along section 232 that is highly flexible and yet maintains a linear change in stiffness as shown in the graph of FIG. 33. Not only is parabolic distal section 232 flexible, but it has a linear change in stiffness thereby providing excellent torque and tactile feedback to the physician when advancing the guidewire through tortuous anatomy. A tapered section 234 that is not curvilinear (not a parabolic grind section) is located on the guidewire 230 distal of the parabolic distal section 232 and it provides reduced bending stiffness and a linear change in bending stiffness as shown in the graph of FIG. 33.

Bending stiffness can be measured in a variety of ways. Typical methods of measuring bending stiffness include extending a portion of the sample to be tested from a fixed block with the sample immovably secured to the fixed block and measuring the amount of force necessary to deflect the end of the sample that is away from the fixed block a predetermined distance. A similar approach can be used by fixing two points along the length of a sample and measuring the force required to deflect the middle of the sample a fixed amount. Those skilled in the art will realize that a large number of variations on these basic methods exist including measuring the amount of deflection that results from a fixed amount of force on the free end of a sample, and the like. Other methods of measuring bending stiffness may produce values in different units of different overall magnitude, however, it is believed that the overall shape of the graph will remain the same regardless of the method used to measure bending stiffness.

Figure 35:
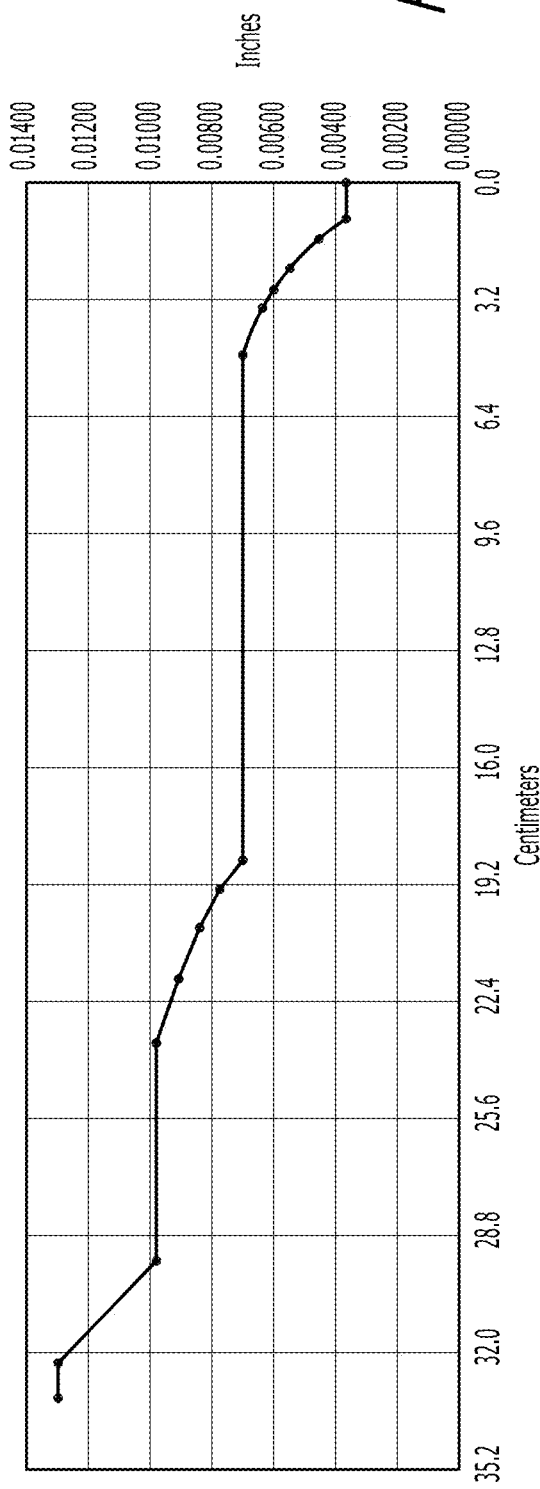
FIG. 35 is a graph of a 0.014 inch diameter guidewire depicting a distal section having a parabolic grind profile.
Figure 36:
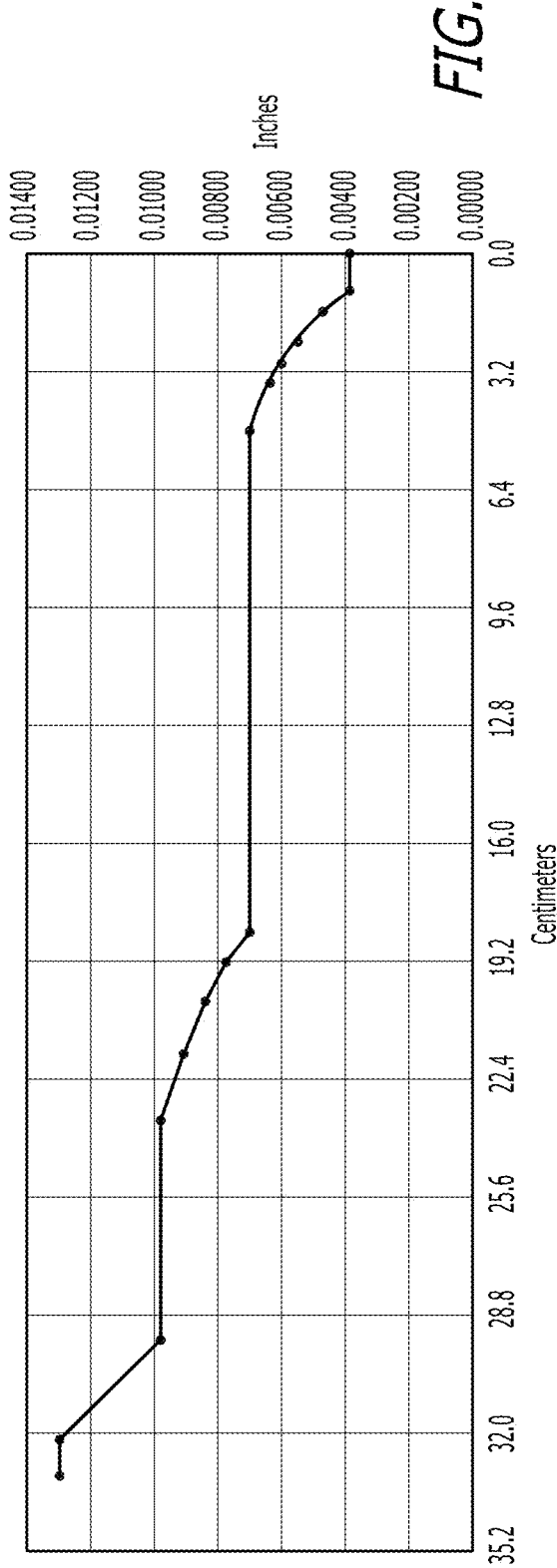
FIG. 36 is a graph of a 0.014 inch diameter guidewire depicting a distal section having a parabolic grind profile.

The parabolic grind profiles for a 0.014 inch diameter guidewire are shown in FIGS. 35 and 36 respectively. The guidewire in FIG. 35 has an 11 gram tip load and the guidewire in FIG. 36 has a 14 gram tip load. The unit of measure on the Y-axis is in inches and the X-axis is in centimeters. In both FIGS. 35 and 36, two parabolic grind profiles are separated by a uniform diameter core wire segment. More specifically, each graph shows a first parabolic grind profile starting at approximately 23.1 cm from the distal tip of the guidewire and ending at approximately 17.9 cm from the distal tip. Further, each graph shows a second parabolic grind starting at approximately 4.8 cm from the distal tip. The uniform diameter core wire section is between the parabolic grind sections, and there is a uniform diameter core wire section starting at approximately 1.2 cm from the distal tip. The parabolic grind profile shown in FIGS. 35 and 36 provide guidewires that have a linear change in stiffness, are flexible, and still maintain a high degree of torque to the guidewire distal end to navigate tortuous arteries and other vessels.

Conventional materials and manufacturing methods may be used to form the parabolic grind profiles of the disclosed guidewires. Those skilled in the art can use computerized grinding machines to form the parabolic grind profiles disclosed herein.

While the invention has been illustrated and described herein in terms of its use as a guidewire, it will be apparent to those skilled in the art that the guidewire can be used in all vessels in the body. All dimensions disclosed herein are by way of example. Other modifications and improvements may be made without departing from the scope of the invention.

I claim:

1. A mold for forming a solder joint, comprising:
  a mold having a cavity configured to receive a distal end of a guidewire and a distal end of a coil having at least one wire coil;
  the cavity defining a volume for receiving solder and heating the solder to form molten solder;
  the mold being formed of a material able to withstand the temperature required to receive the molten solder;
  the cavity defining a specific geometry for receiving the distal end of the guidewire and the distal end of the at least one wire coil into the cavity and cooling the molten solder to form a solder joint; and
  a material surrounding at least a portion of the coil not inserted into the cavity.

2. The mold of claim 1, wherein the specific geometry of the cavity has any of a bullet shape, a micro-J shape, a cone shape, a truncated cone-shape, or a textured surface.

3. The mold of claim 2, wherein the mold is a split mold having a first face and a second face to form the cavity.

4. The mold of claim 3, wherein the split mold first face is a mirror image of the second face.

5. The mold of claim 4, wherein the material includes a thermally conductive material being positioned around the at least one wire coil just above the mold cavity to prevent solder from flowing into wire coils extending outside of the cavity.

6. A method for forming a solder joint, comprising:
  providing a mold having a cavity, wherein the mold is a split mold having a first face and a second face to form the cavity;
  removably attaching the first face to the second face and placing solder material into the cavity;
  heating solder in the cavity by placing the mold in a heating apparatus and heating the mold until the solder becomes molten;
  submerge a distal end of a guidewire into the molten solder in the cavity;
  cooling the mold to solidify the solder and form a solder joint at the distal end of the guidewire;
  after cooling the mold to solidify the solder, split open the mold by separating the first face and the second face; and
  removing the solder joint and guidewire from the mold.

7. The mold of claim 1, wherein the mold is formed from a ceramic material.

8. The method of claim 6, wherein the first face and the second face are mirror images of each other.

9. The method of claim 8, wherein a wire coil has a proximal end and a distal end, the wire coil being disposed on the distal end of the guidewire, further comprising:

forming the solder joint to join the distal end of the wire coil and distal end of the guidewire.

10. The method of claim 9, wherein the wire coil includes a plurality coils, further comprising:
positioning the distal end of the wire coil so that no more than four coils are submerged into the molten solder.

11. The method of claim 10, wherein the cavity has any of a bullet shape, a micro-J shape, a cone shape, a truncated cone-shape, or a textured surface.

* * * * *